(12) United States Patent
Mani et al.

(10) Patent No.: US 10,933,104 B2
(45) Date of Patent: *Mar. 2, 2021

(54) GUT BARRIER DYSFUNCTION TREATMENT AND PREVENTION

(71) Applicant: Albert Einstein College of Medicine, Bronx, NY (US)

(72) Inventors: Sridhar Mani, Riverdale, NY (US); Subhajit Mukherjee, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 408 days.

This patent is subject to a terminal disclaimer.

(21) Appl. No.: 15/901,919

(22) Filed: Feb. 22, 2018

(65) Prior Publication Data

US 2018/0185422 A1 Jul. 5, 2018

Related U.S. Application Data

(63) Continuation of application No. 14/729,211, filed on Jun. 3, 2015, now Pat. No. 9,925,222, which is a continuation-in-part of application No. PCT/US2013/072709, filed on Dec. 3, 2013.

(60) Provisional application No. 61/777,084, filed on Mar. 12, 2013, provisional application No. 61/734,487, filed on Dec. 7, 2012.

(51) Int. Cl.

| | | |
|---|---|---|
| A61K 35/74 | (2015.01) | |
| A61K 31/405 | (2006.01) | |
| A61K 35/742 | (2015.01) | |
| C07D 211/56 | (2006.01) | |
| C07D 211/92 | (2006.01) | |
| G16H 50/20 | (2018.01) | |
| G06F 19/00 | (2018.01) | |
| A61K 35/741 | (2015.01) | |
| C12Q 1/02 | (2006.01) | |
| A61K 35/00 | (2006.01) | |

(52) U.S. Cl.
CPC .......... *A61K 35/742* (2013.01); *A61K 35/741* (2013.01); *C07D 211/56* (2013.01); *C07D 211/92* (2013.01); *C12Q 1/025* (2013.01); *G06F 19/00* (2013.01); *G16H 50/20* (2018.01); *A61K 2035/115* (2013.01); *Y02A 90/10* (2018.01); *Y10T 436/145555* (2015.01)

(58) Field of Classification Search
None
See application file for complete search history.

(56) References Cited

U.S. PATENT DOCUMENTS

| | | |
|---|---|---|
| 5,374,543 A | 12/1994 | Murdock |
| 8,168,656 B2 | 5/2012 | Marnett et al. |
| 2014/0234260 A1 | 8/2014 | Borody |
| 2017/0067065 A1 | 3/2017 | Falb et al. |

OTHER PUBLICATIONS

Li et al., Indole production by the tryptophanase TnaA in *Escherichia coli* is determined by the amount of exogenous tryptophan Microbiology (2013), 159, 402-410.*
Wikoff et al., Metabolomics analysis reveals large effects of gut microflora on mammalian blood metabolites 3698-3703 PNAS Mar. 10, 2009, vol. 106, No. 10.*
Yanofsky et al., RNA-based regulation of genes of tryptophan synthesis and degradation, in bacteria RNA (2007), 13:1141-1154.*
Chaturvedi A et al. Incidence of spore fanning Clostridium sporogenes in different dairy products and their industrial and public health significance. The Pharma Innovation Journal 2015; 3(11): 30-32.*
PCT International Search Report and Written Opinion, dated Mar. 10, 2014 in connection with PCT International Application No. PCT/US2013/72709, 12 pages.
Dou W et al., entitled "Alleviation of Gut Inflammation by Cdx2/Pxr Pathway in a Mouse Model of Chemical Colitis," PlosOne, Jul. 16, 2012, vol. 7, No. 7:e36075, pp. 1-13.
Bansal T et al., entitled "The Bacterial Signal Indole Increases Epithelial-Cell Tight-Junction Resistance and Attenuates indicators of Inflammation," PNAS, Dec. 4, 2009, vol. 107, No. 1, pp. 228-233.
Zavisic G. et al., entitled "Probiotic Features of Two Oral Lactobacillus isolates," Brazillian Journal of Microbiology, Jan. 2012, vol. 43, No. 1, pp. 418-428.
Wang H et al., entitled "Pregnane X Receptor Activation Induces FGF19-Dependent Tumor Aggressiveness In Humans and Mice," Journal of Clinical Investigation, Jul. 11, 2011, vol. 121, No. 8, pp. 3220-3232.
Venkatesh M et al., entitled "Symbiotic Bacterial Metabotites Regulate Gastrointestinal Barrier Function via the Xenobiotic Sensor PXR and Toll-like Receptor 4," Immunity 41, 296-310, Aug. 21, 2014. Epub Jul. 24, 2014.
Dring A M et al., entitled "Rational Quantitative Structure-Activty Relationship (RQSAR) Screen for PXR and CAR Isoform-Specific Nuclear Receptor Ligands," Chem Biol Interact., Dec. 5, 2010; 188(3): 512-525.
Ölgen S et al., entitled "Synthesis and biological evaluation of N-substituted indole esters as inhibitors of cyclo-oxygenase-2 (COX-2)," II Farmaco 57 (2002) pp. 677-683.
Poljsak B at al., entitled "Achieving the Balance between ROS and Antioxidants: When to Use the Synthetic Antioxidants," Oxidative Medicine and Cellular Longevity, vol. 2013, Article ID 956792, 11 pages.
Shimada Y et al., entitled "Commensal Bacteria-Dependent Indole Production Enhances Epithelial Barrier Function in the Colon," PLOS ONE, Nov. 2012, vol. 8, Issue 11, e80604, pp. 1-10.
Valenzano M C et al., entitled "Remodeling of Tight Junctions and Enhancement of Barrier Integrity of the CACO-2 Intestinal Epithelial Cell Layer by Micronutrients," PLOS ONE 10(7): e0133926, pp. 1-22.

(Continued)

*Primary Examiner* — Maria G Leavitt
(74) *Attorney, Agent, or Firm* — Fox Rothschild LLP

(57) ABSTRACT

Methods are disclosed for treating and preventing gut barrier dysfunction or an illness associated with gut barrier dysfunction in a subject comprising administering to the subject bacterium that produce an indole or an indole metabolite and for identifying compounds and bacteria for use in treatment and prevention of gut barrier dysfunction or an illness associated with gut barrier dysfunction.

16 Claims, 16 Drawing Sheets

Specification includes a Sequence Listing.

(56) References Cited

OTHER PUBLICATIONS

Blumberg B et al. "Orphan nuclear receptors—new ligands and new possibilities," Genes & Development 12:3149-3155, 1998.
Capelli D et al "Structural basis for PPAR partial or full activation revealed by a novel ligand binding mode," Science Reports, 6:34792, pp. 1-12, 2016.
Chaturvedi A et al. Incidence of spore forming Clostridium sporogenes in different dairy products and their industrial and and public health significance. The Pharma Innovation Journal 2015: 3(11):30-32.
Dring Am et al. "Rational quantitative structure-activity relationship (RQSAR) screen for PXR and CAR isoform-specific nuclear receptor ligands." Chem. Biol. Interact. Dec. 5, 2010: 188(3):512-525.
Fakhrudin N et al. "Computer-aided discovery, validation, and mechanistic characterization of novel neolignan activators of peroxisome proliferator-activated receptor γ". Mol. Pharmacol. 77:559-565, 2010.
Guo D et al. "Induction of nuclear translocation of constitutive androstane receptor by peroxisome by proliferator-activated receptor α synthetic ligands in mouse liver." The Journal of Biological Chemistry, vol. 282, No. 50, pp. 36766-36776, 2007.
Hubbard TD et al. "Adaptation of the human aryl hydrocarbon receptor to sense microbiota-derived indoles," Science Reports, 5:12689, 2015.
Lannutti F et al. "Estimation of the PPARα agonism of fibrates by a combined MM-docking approach." Chapter 17 in Methods and Protocols, Methods in Molecular Biology, vol. 952, Springer Science+Business Media, New York, 2013.
Navaratnarajah P et al. "Rifampicin-independent interactions between the pregame X receptor ligand binding domain and peptide fragments of coactivator and corepressor proteins." Biochemistry 2012, 50, 19-31.
Patel RD et al. "Aryl-Hydrocarbon receptor activation regulates constitutive androstane receptor levels in murine and human liver." Hepatology, 2007 46(1):209-218.
Ranhotra HS et al. "Xenobiotic receptor-mediated regulation of intestinal barrier function and innate immunity." Nuclear Receptor Research, vol. 3, (2016), Article ID 101199, pp. 1-19.
Xiao L et al. "Roles of xenobiotic receptors in vascular pathophysiology." Circulation Journal vol. 78: 1520-1530, 2014.
Zhang Y-M et al. "Insilico investigation of agonist activity of a structurally diverse set of drugs to hPXR using HM-BSM and HM-PNN." J. Huazhong Univ. Sci. Teohnol. [Med Sci] 36(3):463-468, 2016.
Gronemeyer H, et al. "Principles for modulation of the nuclear receptor superfamily." Nat. Rev. Drug Discov. 11: 950-964, 2004 (Abstract only).
Naduri R, et al. "ONRLDB-manually curated database of experimentally validated ligands for orphan nuclear receptors: insights into new drub discovery." Database (2015), vol. 2015, article ID bav112, 16 pages.
Attwood, G et al., entitled "Production of indolic compounds by rumen bacteria isolated from grazing ruminants," Journal of Applied Microbiology, 100 (2006), pp. 1261-1271.
Chen, Y et al., entitled "Nuclear receptors in the multidrug resistance through the regulation of drug-metabolizing enzymes and drug transporters," Biochem Pharmacol, Apr. 15, 2012; 83(8): pp. 1112-1116.
Jin, U H et al., entitled "Microbiome-Derived Tryptophan Metabolites and Their Aryl Hydrocarbon Receptor-Dependent Agonist and Antagonist Activities," Molecular Pharmacology, 85:777-785, May 2014.
Li, G et al., entitled "Indole production by the tryptophanase TnaA in *Escherichia coli* is determined by the amount of exogenous tryptophan," Microbiology (2013). 159, pp. 402-410.
Mani S, entitled "Chapter 23, Regulation of host chromatin by bacterial metabolites. In:Binda O and Fernandez-Zapico ME (eds) Chromatin Signaling and Diseases," 1st Edition, Academic Press, 2016, pp. 423-442.
Wikoff, W R et al., entitled "Metabolomics analysis reveals large effects of gut microflora on mammalian blood metabolites," PNAS, Mar. 10, 2009, vol. 106, No. 10. pp. 3098-3703.
Yanofsky, C et al., entitled "RNA-based regulation of genes of tryptophan synthesis and degradation, in bacteria," RNA (2007), 13:1141-1154.
Zelante, T et al., entitled "Ttryptophan Catabolites from Microbiota Engage Aryl Hydrocarbon Receptor and Balance Mucosal Reactivity via Interleukin-22," Immunity 39, pp. 372-385, Aug. 22, 2013.
Mackowiak B et al., entitled "Molecular basis of metabolism-mediated conversion of PK11195 from an antagonist to an agonist of the constitutive androstane receptor," Molecular Pharmacology Fast Forward, published on Apr. 25, 2017 as DOI: 10.1124/mol. 117.108621. Downloaded from molpharm.aspetjournals.org at ASPET Journals on Apr. 27, 2017, 44 pages.
Brave et al., "Microbial controles of intestinal innate immunity." Oncotarget, vol. 6, No. 24, 2015, 19961-19963.
Gong et al., The mechanism of tryptophan induction of tryptophanase operon expression: Tryptophan inhibits release factor-mediated cleavage of TnaC-peptidyl-tRNAProPNAS u Jul. 31, 2001 u vol. 98 u No. 16 u 8997-9001.
Nanduri et al., "ONRLDB—manually curated database of experimentally validated ligands for orphan nuclear receptors: insights into new drug discovery," Database, 2015, 1-16.
Santos et al. "Role of mast cells in chronic stress induced colonic epithelial barrier dysfunction in the rat," Gut, 2001;48:630-636.
Satsu et al., "Activation of Pregnane X Receptor and induction of MDR1 by Dietary Phytochemicals," J. Agric. Food Chem., 2008, 56, 5366-5373.
Jantschko et al., "Exploitation of the unusual thermodynamic properties of human myeloperoxidase in inhibitor design," Biochem Pharmacol., Apr. 15, 2005;69(8):1149-57, (abstract).
Moco et al., Systems Biology Approaches for Inflammatory Bowel Disease: Emphasis on Gut Microbial Metabolism Future Directions and Methods in IBD Research, 2014, pp. 2104-2114.
Jellet et al., "Production of indole-3-proparioic acid and 3-(p-hydroxyphenyl)propanoic acid by Clostridium sporogenes: a convenient thin-layer chromatography detection system," Canadian Journal of Microbiology, 1980, vol. 26, No. 4: pp. 448-453. Abstract.
Lemaire et al., "Identification of New Human Pregnane X Receptor Ligancis among Pesticides Using a Stable Reporter Cell System," Toxicological Sciences 91 (2), 501-509, (2006).
Waxman et al., "MiniReview P450 Gene Induction by Structurally Diverse Xenochemicals: Central Role of Nuclear Receptors CAR, PXR, and PPAR1," Archives of Biochemistry and Biophysics, vol. 369, No. 1, Sep. 1, pp. 11-23, 1999.

\* cited by examiner

GUT BARRIER DYSFUNCTION TREATMENT AND PREVENTION

CROSS-REFERENCE TO RELATED APPLICATIONS

This application is a continuation application of application No. 14/729,211, filed on Jun. 3, 2015, now U.S. Pat. No. 9,925,222, which is a continuation-in-part of and claims priority of PCT International Patent Application No. PCT/US2013/072709, filed Dec. 3, 2013, which designates the United States of America and which claims the benefit of U.S. Provisional Patent Application No. 61/777,084, filed on Mar. 12, 2013, and of U.S. Provisional Patent Application No. 61/734,487, filed on Dec. 7, 2012, the contents of all of which are incorporated herein by reference in their entireties.

STATEMENT OF GOVERNMENT SUPPORT

This invention was made with government support under grant number CA127231 awarded by the National Institutes of Health. The government has certain rights in the invention.

FIELD OF THE INVENTION

The invention relates to activation of the pregnane X receptor (PXR) as a means of preventing or alleviating toxic or inflammatory injury to the intestines, and treating the "leaky" intestinal (gut) syndrome, using for example, colonization of the gut with bacteria that produce indoles that activate PXR. The invention further provides a method of identifying compounds for treating or preventing leaky gut syndrome by determining if the compound activates PXR.

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

Gut barrier dysfunction is linked to a broad spectrum of human ailments (1-5). Increased permeability of the gut wall can result, for example, from toxins, poor diet, parasites, infection, or medications (5). Leaky gut syndrome is a term for enhanced intestinal permeability, which can occur in patients susceptible to a multitude of diseases ranging, for example, from inflammatory bowel disease to autoimmune systemic ailments. Patients who develop dysbiosis or bacterial overgrowth, or who are on long-term antibiotics or are generally susceptible to inflammatory diseases of the gut are likely to have enhanced intestinal permeability as a pathogenic cause driving future associations with disease onset. Orphan nuclear receptors may serve as a link between the host environment and gut immunity. One such receptor is the pregnane X receptor (PXR) (NR1I2; also termed SXR, PAR). PXR is the primary xenobiotic sensor in human and mammalian tissues. It responds to a wide range of structurally- and chemically-distinct ligands (52-62).

The present invention addresses the need for methods of treating and preventing gut barrier dysfunction and illnesses associated with gut barrier dysfunction, such as inflammatory bowel disease, cardiovascular, pulmonary or autoimmune disease.

SUMMARY OF THE INVENTION

The invention provides methods of treating or preventing gut barrier dysfunction or an illness associated with gut barrier dysfunction or toxic or inflammatory injury to intestines or leaky intestinal (gut) syndrome in a subject comprising administering to the subject bacterium that produce an indole or an indole metabolite.

The invention also provides probiotic oral supplements comprising a commensal bacterium that produce indole or an indole metabolite for treating or preventing gut barrier dysfunction or an illness associated with gut barrier dysfunction or toxic or inflammatory injury to intestines or leaky intestinal (gut) syndrome.

The invention further provides methods of identifying a compound or a bacterium as a candidate for treating or preventing gut barrier dysfunction or an illness associated with gut barrier dysfunction or toxic or inflammatory injury to intestines or leaky intestinal (gut) syndrome comprising determining whether or not the compound activates pregnane X receptor (PXR) or the bacterium produces a compound that activates PXR, wherein a compound that activates PXR or a bacterium that produces a compound that activates PXR is a candidate for treating or preventing gut barrier dysfunction or an illness associated with gut barrier dysfunction or toxic or inflammatory injury to intestines or leaky intestinal (gut) syndrome and wherein a compound that does not activate PXR or a bacterium that does not produce a compound that activates PXR is not a candidate for treating or preventing gut barrier dysfunction or an illness associated with gut barrier dysfunction or toxic or inflammatory injury to intestines or leaky intestinal (gut) syndrome.

The invention also provides a method of determining whether or not a subject has inflammation, the method comprising experimentally determining the levels of indole-3-propionic acid (IPA) and tryptophan from a sample from the subject, and calculating the ratio of levels of indole-3-propionic acid (IPA)/tryptophan, wherein a low ratio is indicative of inflammation and a high ratio is indicative of no inflammation.

DETAILED DESCRIPTION OF THE INVENTION

Figures 1A, 1B, 1C, 1D, 1E, 1F, 1G, 1H:
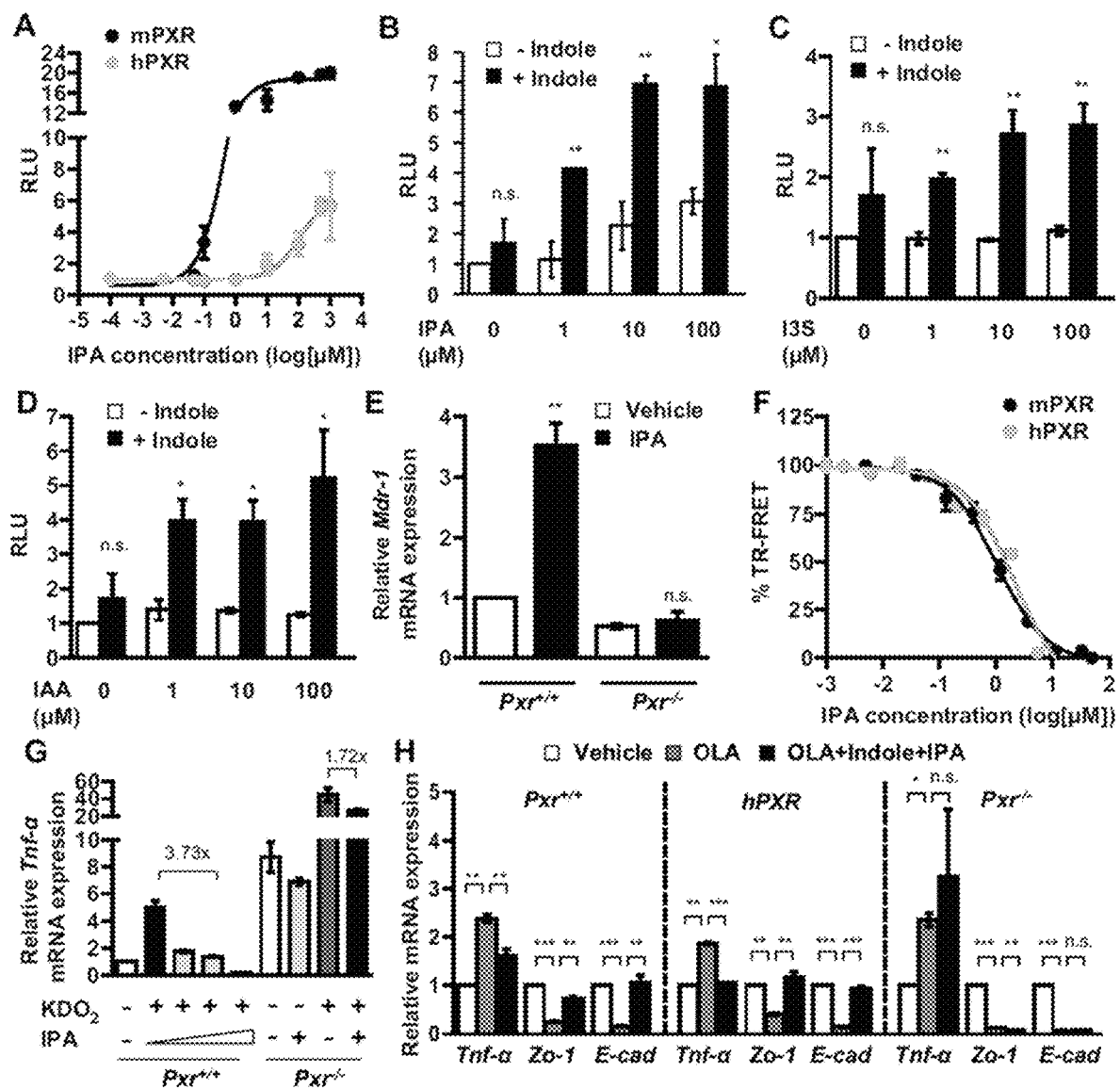
FIG. 1A-1H. Gut commensal derived indole metabolite, IPA regulates PXR activation. (A) Transcriptional activity of a PXR reporter gene (multi-drug resistance-associated protein 2 or MRP2 luciferase) co-transfected with mPXR and hPXR expression plasmids in 293T cells following treatment with IPA (n=3). RLU, relative light unit. Data expressed as fold change in RLU compared to vehicle (DMSO) controls. (B to D) Transcriptional activity of a PXR reporter gene (MRP2 luciferase) co-transfected with hPXR expression plasmid in 293T cells following treatment with fixed concentration of indole (1 mM) and increasing concentrations of IPA (B), I3S (C) and IAA (D) (n=3). RLU, relative light unit. Data expressed as fold change in RLU compared to vehicle (DMSO) controls. (E) Real-time qPCR analysis of Mdr-1 expression in $Pxr^{+/+}$ and $Pxr^{-/-}$ mice jejunum apical enterocytes following oral treatment with IPA (20 mg/kg) (n=5 mice per group). (F) In vitro TR-FRET PXR competitive binding assay with mPXR and hPXR following treatment with IPA. (G) Expression of Tnf-_ in Pxr+/+ and Pxr−/− mice jejunum apical enterocytes following treatment with KDO2 (200 µg/mice) and oral IPA (10, 20 and 40 mg/kg) was analyzed by real-time qPCR (n=5 mice per group). IPA (20 mg/kg) decreases epithelial Tnf-_ mRNA expression more in Pxr$^{+/+}$ compared to Pxr−/− mice (3.73 fold vs. 1.72 fold). (H) Real-time qPCR analysis of Tnf-α, Zo-1 and E-cad expression in Pxr$^{+/+}$, hPXR and Pxr$^{−/−}$ mice jejunum apical enterocytes following treatment with OLA (5 mg/ml), indole (1 mM) and IPA (1 µM) (n=5 mice per group). All graphs show mean values±s.e.m. *P≤0.05; P≤0.01; *P≤0.001, n.s. not significant.

The invention provides a method of treating or preventing gut barrier dysfunction or an illness associated with gut barrier dysfunction or toxic or inflammatory injury to intestines or leaky intestinal (gut) syndrome in a subject comprising administering to the subject bacterium that produce an indole or an indole metabolite.

As used herein, "treating" or "treat" a condition means to alleviate or ameliorate or eliminate a sign or symptom of the condition that is being treated. "Preventing" or "prevent" a condition means that in a subject who is free of the condition, reducing the risk of the subject developing the condition or reducing the severity of the condition that the subject develops compared to the severity of the condition that would develop in the absence of administering to the subject bacterium that produce an indole or an indole metabolite.

Preferably, the bacterium colonize the gut of the subject. Examples of bacterium that can be used include *Clostridium sporogenes*.

Examples of indoles include indole-3-propionic acid and indoleacetic acid. Preferably, the indole activates the pregnane X receptor (PXR).

The subject can have, for example, irritable bowel syndrome, inflammatory bowel disease, intestinal allergic syndrome or celiac sprue. The subject can be at risk for developing gut barrier dysfunction or an illness associated with gut barrier dysfunction due to, for example, exposure to a toxin, a medication, poor diet, an infection such as a parasite infection or a bacterial infection, dysbiosis, bacterial overgrowth, or long-term use of an antibiotic.

In an embodiment, the bacterium is a recombinant bacterium genetically engineered to constitutively-express an indole-producing enzyme. In a preferred embodiment, the indole-producing enzyme is a tryptophanase. In a preferred embodiment, the tryptophanase is an *E. Coli* tryptophanase. In an embodiment, the bacterium is an *E. coli*. In an embodiment, the recombinant bacterium comprises a tnaC knockout. In an embodiment, the recombinant bacterium comprises a rut gene knockout. In an embodiment, the recombinant bacterium comprises a boxA mutation. In an embodiment, the boxA mutation comprises a deletion of the sequence CGC CCT in boxA.

Preferably, the bacterium is administered orally to the subject. Bacteria can be cultured and reconstituted in common drinkables, e.g., yogurt as probiotic supplementation for conditions where, for example, there is a high risk for leaky gut, such as, e.g., irritable bowel syndrome, inflammatory bowel disease, intestinal allergic syndrome, celiac sprue, or prolonged antibiotic use.

The subject can be any animal and is preferably a human.

The invention also provides a probiotic oral supplement comprising a commensal bacterium that produces indole or an indole metabolite for treating or preventing gut barrier dysfunction or an illness associated with gut barrier dysfunction or toxic or inflammatory injury to intestines or leaky intestinal (gut) syndrome. Examples of such bacterium include *Clostridium sporogenes*. In an embodiment, the bacterium is a recombinant bacterium genetically engineered to constitutively-express an indole-producing enzyme. In a preferred embodiment, the indole-producing enzyme is a tryptophanase. In a preferred embodiment, the tryptophanase is an *E. Coli* tryptophanase. In an embodiment, the bacterium is an *E. coli*. In an embodiment, the recombinant bacterium comprises a tnaC knockout. In an embodiment, the recombinant bacterium comprises a rut gene knockout. In an embodiment, the recombinant bacterium comprises a boxA mutation. In an embodiment, the boxA mutation comprises a deletion of the sequence CGC CCT in boxA.

The invention also provides a method of identifying a compound or a bacterium as a candidate for treating or preventing gut barrier dysfunction or an illness associated with gut barrier dysfunction or toxic or inflammatory injury to intestines or leaky intestinal (gut) syndrome comprising experimentally determining whether or not the compound activates pregnane X receptor (PXR) or the bacterium produces a compound that activates PXR, wherein a compound that activates PXR or a bacterium that produces a compound that activates PXR is a candidate for treating or preventing gut barrier dysfunction or an illness associated with gut barrier dysfunction or toxic or inflammatory injury to intestines or leaky intestinal (gut) syndrome and wherein a compound that does not activate PXR or a bacterium that does not produce a compound that activates PXR is not a candidate for treating or preventing gut barrier dysfunction or an illness associated with gut barrier dysfunction or toxic or inflammatory injury to intestines or leaky intestinal (gut) syndrome. As used herein, the step of "determining" requires an experimental determination that involves the use of a machine and/or involves a physical and/or chemical transformation.

Methods for determining that a compound or compounds activate PXR include, for example, cell based assays (using transient or stable PXR expressing reporter systems), whole animal based assays in which there is either a functional (e.g., luciferase or GFP reporter), drug/compound kinetic (e.g., compound pharmacology suggesting PXR mediated metabolism), and/or genetic (e.g., PXR target gene assessments) or cell biology based (e.g., protein localization or binding) readout, biochemical (radio-ligand based assays, structural studies with protein-ligand complexes, thermal or chemical denaturation studies, electrophysiochemical approaches), and other assays that combine one or more of these components. The method can comprise transfecting a cell with nucleic acid that expresses PXR. Preferably, the cell is transfected with nucleic acid that expresses human PXR. A method comprising any study that uses PXR readout either biochemical or cell based, is appropriate to claim that a compound activates PXR.

Human PXR has the amino acid sequence (SEQ ID NO:20, Accession: O75469.1 GI: 6093860)

```
  1  mevrpkeswn  hadfvhcedt  esvpgkpsvn  adeevggpqi  crvcgdkatg  yhfnvmtceg 61  ckgffrramk  rnarlrcpfr  kgaceitrkt  rrqcqacrlr  kclesgmkke  mimsdeavee 121  rralikrkks  ertgtqplgv  qglteeqrmm  irelmdaqmk  tfdttfshfk  nfrlpgvlss 181  gcelpeslqa  psreeaakws  qvrkdlcslk  vslqlrgedg  svwnykppad  sggkeifsll 241  phmadmstym  fkgiisfakv  isyfrdlpie  dgisllkgaa  felcqlrfnt  vfnaetgtwe 301  cgrlsycled  taggfqqlll  epmlkfhyml  kklqlheeey  vlmqaislfs  pdrpgvlqhr 361  vvdqlqeqfa  itlksyiecn  rpqpahrflf  lkimamltel  rsinaqhtqr  llriqdihpf 421  atplmqelfg  itgs.
```

Examples of cell lines can be used include Caco-2, LS174T, 293T, HepG2, SKOV-3 and LS174T cells.

An in vitro transcription assay is described herein. As described in U.S. Patent Application Publication No. US 2011/0105522, published May 5, 2011, the contents of which are incorporated herein by reference, PXR activation has been shown to induce PXR target genes in SKOV-3 ovarian cancer cells. Gene expression can be evaluated using quantitative RT-PCR. In addition, PXR activation induces SKOV-3 cell proliferation in vitro and in vivo. PXR activation also induces multi-drug resistance in SKOV-3 cells. PXR activation in LS174T cells induces cell proliferation. In addition, pregnane X receptor activation has been shown to induce FGF19-dependent tumor aggressiveness in humans and mice (49).

The compound being evaluated can be, for example, an indole derivative, an indole analog or an indole metabolite. The compound can be, for example, a metabolite, bacterial product or food substance that is derived from tryptophan or from an indole base. The bacterium can produce indole or an indole metabolite.

The inventions also provides a method of determining whether or not a subject has intestinal inflammation, the method comprising experimentally determining the levels of indole-3-propionic acid (IPA) and tryptophan from a sample from the subject, and calculating the ratio of levels of indole-3-propionic acid (IPA)/tryptophan, wherein a low ratio is indicative of intestinal inflammation in the subject and a high ratio is indicative of no intestinal inflammation in the subject. The sample can be, for example, a blood sample or a stool sample. The ratio of levels of indole-3-propionic acid (IPA)/tryptophan serves as an indicator or biomarker for intestinal inflammation. In one embodiment, an IPA/tryptophan ratio less than 1 indicates intestinal inflammation in the subject. In one embodiment, an IPA/tryptophan ratio greater than 1 indicates no intestinal inflammation in the subject.

Methods to determine tryptophan and tryptophan metabolites, particularly indoles and IPA, include, for example, chromatographic separation assays, liquid or solid chromatography, fluorescence, mass spectrometry and/or a combination of these methods.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Example A

Introduction

To test the hypothesis that elements of the host environment, including symbiotic bacteria, regulate gut barrier function through the pregnane x receptor (PXR), the functions of indole metabolites (e.g., indole-3-propionic acid (IPA)), which are exclusively produced by gut commensal microbes (6) were explored. In mice, IPA synthesis appears linked to the gut commensal *Clostridium sporogenes* (6). In humans under homeostatic conditions, blood IPA and indole concentrations remain in micromolar and millimolar range, respectively, with gut concentrations predicted to be much higher (7, 8).

Example 1

Materials and Methods

Cell Lines, Human Tissue Samples and Reagents.

The human colon cancer cell lines (Caco-2 and LS174T) and 293T cells were obtained from the American Type Culture Collection (ATCC) and cultured according to ATCC recommendations. DMSO, indole, IPA, I3 S, IAA, FITC-dextran, indomethacin, and LPS were obtained from Sigma Aldrich; DSS from MP Biomedicals; Hematoxylin and Eosin stain from Poly Scientific; BrdU from Becton Dickinson, anti-CD3 antibody from BD biosciences; $KDO_2$ from Avanti Polar Lipids Inc. TLR2 inhibitory antibody from eBioscience (14-9024-82) and TLR4 inhibitor from Invivogen. For immunoblotting, antibodies used are as indicated: TLR4 (Santa Cruz, sc-16240), alkaline phosphatase (Santa Cruz, sc-30203), β-actin (Abcam, ab8227), p-p38-MAPK (Cell Signaling, 9215), p38-MAPK (Cell Signaling, 9212), p-ERK (Santa Cruz, sc-7383), ERK (Santa Cruz, sc-93), p-JNK (Cell Signaling, 9251), JNK (Cell Signaling, 9252), p-IB-α (Cell Signaling, 9246), IKB-α (Cell signaling, 9242). Antibodies used for immunostaining are mentioned in appropriate section. For TLR4 transcription assay, 293T cells were co-transfected with PXR expression plasmid, PU.1 expression plasmid and TLR4 promoter luciferase construct (kindly provided by Dr. Michael Rehli of University Hospital Regensburg, Regensburg, Germany).

Mice.

All animal experiments were approved by the animal institute committee (protocol #20070715, 20100711) of the Albert Einstein College of Medicine and were performed in accordance with institutional and national guidelines. $Pxr^{+/+}$ wild-type C57BL/6 mice (6-8 week old) were purchased from Jackson laboratory. Swiss Webster (SW, control) and Swiss Webster Germfree (SWGF) mice (7-8 weeks old, female) were purchased from Taconic (Hudson, N.Y.). $Pxr^{-/-}$ and humanized PXR transgenic mice (hPXR) mice were kindly provided by Dr. Jeff Staudinger (University of Kansas) and Dr. Wen Xie (University of Pittsburgh), respectively. $Pxr^{-/-}$ mice were crossed with $Tlr4^{-/-}$ mice (purchased from Jackson laboratory, stock no. 007227) to generate $Pxr^{-1}7 Tlr4^{-/-}$ double knockout mice. All mice were sex and age matched within experiments, and maintained under a strict 12 hour light/dark cycle with free access to sterilized chow and water.

Genotyping.

Mouse tail DNAs were used for genotyping according to manufacturer's instructions (DNeasy Blood and Tissue kit, Qiagen). The primers used for Pxr genotyping were:

```
Forward primer:
                                        (SEQ ID NO: 1)
5'-CTGGTCATCACTGTTGCTGTACCA-3';

Reverse primer 1:
                                        (SEQ ID NO: 2)
5'-GCAGCATAGGACAAGTTATTCTAGAG-3';

Reverse primer 2:
                                        (SEQ ID NO: 3)
5'-CTAAAGCGCATGCTCCAGACTGC-3'.

The following primers were used for Tlr4 geno-
typing:
Forward primer (wild-type):
                                        (SEQ ID NO: 4)
5'-ATATGCATGATCAACACCACAG-3';

Reverse primer (wild-type):
                                        (SEQ ID NO: 5)
5'-TTTCCATTGCTGCCCTATAG-3';

Forward primer (knockout):
                                        (SEQ ID NO: 6)
5'-GCAAGTTTCTATATGCATTCTC-3';

Reverse primer (knockout):
                                        (SEQ ID NO: 7)
5'-CCTCCATTTCCAATAGGTAG-3'.
```

For Pxr genotyping the following PCR conditions were used: 94° C. for 3 minutes, and then each cycle at 94° C. for 30 seconds, 60° C. for 1 minute, 72° C. for 1 minute, repeated for 38 cycles. The final cycle extension time was 2 minutes. PCR conditions used for Tlr4 genotyping were similar to Pxr genotyping except the annealing temperature, which was set at 55° C. for 1 minute. PCR products were subsequently run on 1% agarose gel for visualization. Genotyping for Pxr$^{-/-}$ and hPXR mice were performed as previously published (29, 30).

Histology and Immunofluorescence Analysis.

Intestinal tissue sections (paraffin and frozen) were prepared and Hematoxylin-Eosin staining were performed in the Histology core facility of Albert Einstein College of Medicine. Histological scoring was performed according to previously published methods (31). Briefly, Hematoxylin-Eosin stained sections were evaluated in a blinded fashion by a trained pathologist at Albert Einstein College of Medicine and quantified in the following manner: 0=normal bowel, 1=epithelial loss confined to villus tip, 2=epithelial detachment from underlying lamina propria, 3=epithelial detachment involving less than half of the villus and 4=epithelial detachment involving more than half of the villus and/or fluid accumulation. For immunofluorescence studies, cryostat intestinal sections of 5 µm thickness were fixed (4% paraformaldehyde in PBS, pH 7.4) and blocked in buffer containing 5% goat serum, 1% BSA and 0.1% Triton X-100 in PBS. Sections were then incubated with primary and secondary antibodies overnight at 4° C. and for 2 h at room temperature, respectively. The following primary antibodies were used for immunofluorescence analysis: Zo-1 (1:100, Zymed, 40-2300) and E-cadherin (1:100, BD biolabs, 610182). Secondary antibodies, conjugated to Alexa Fluor 488, were obtained from Molecular Probes. Microscopy was performed in the Analytical Imaging Facility of Albert Einstein College of Medicine with Biorad Radiance 2000 Laser Scanning Confocal Microscope. Image acquisition was performed using Zeiss Laserscan 2000 software and image processing was performed with NIH ImageJ software.

Isolation of Gut Apical Enterocytes.

The Weiser method was used to isolate pure apical "villus" enterocytes from the jejunum in all mice experiments as previously published (32). Enterocytes isolated were subsequently pooled for down-stream experiments.

In Vitro Transcription Assay.

These assays were performed in 293T cells as previously published (33). In brief, transient transfection by lipofectamine (Invitrogen) were carried out in 293T cells with plasmids expressing human PXR (hPXR), mouse PXR (mPXR), GAL4-FXR, GAL4-LXR, GAL4-PPARγ and mouse CAR (mCAR) with respective reporter plasmids (Tk-MRP2-luciferase, Tk-MH100-luciferase, CYP2B10-luciferase) and Renilla. For TLR4 promoter luciferase transcription assay, TLR4 promoter reporter construct (a gift from Dr. Michael Rehli of University of Regensburg, Germany) was transfected along with human PXR, mouse PU.1 expression plasmids and Renilla. 5 h after transfection, indole/IPA/I3 S/IAA, receptor agonists (rifampicin, hPXR ligand, 20 µM; chenodeoxycholic acid, FXR ligand, 50 µM; T0901315, LXR ligand, 5 µM; rosiglitazone, PPARγ ligand, 10 µM; TCPOBOP, mCAR ligand, 0.2 µM) was added to the media and incubated for a total period of 48 h. The cells were harvested in passive lysis buffer (Promega) and luciferase activity was detected using the dualluciferase reporter assay system from Promega in 20 µl of cell lysate using the Turner Biosystems 20/20n Luminometer. Assays were performed at least two independent times each in triplicates.

Time Resolved Fluorescence Resonance Energy Transfer (TR-FRET) Assay.

A LanthaScreen TR-FRET PXR Competitive Binding Assay was conducted according to the manufacturer's protocol (Invitrogen) as previously published (14). Briefly, serial dilutions of indole 3-propionic acid (diluted in TR-FRET PXR Assay Buffer, Invitrogen) were dispensed into triplicate wells of a black, non-treated 384 well plate (Corning Life Sciences). Subsequently, 5 µl of Fluormone PXR Green was added into each well. Finally, 5 µl of a master mix containing hPXR ligand binding domain (LBD), terbium labeled anti-glutathione S transferase (final concentration 10 nM) and dithiothreitol (final concentration 0.05 mM) was added into each well. For mPXR ligand binding domain, GST tagged mPXR LBD was purified using Glutathione Sepharose 4 Fast Flow beads (GE Health Care) in Poly-Prep Chromatography columns (Bio-Rad). hPXR LBD of the assay kit was replaced with the similar concentrations of mPXR LBD. The content was mixed briefly (10 s) and incubated in dark at room temperature for 1 h. TR-FRET was measured using SpectraMaxR M5 microplate reader (Molecular Devices) with the excitation wavelength of 340 nm and emission wavelengths of 520 and 495 nm. TR-FRET ratio was calculated by dividing the emission signal at 520 nm by emission signal at 495 nm. Data are expressed as percentage TR-FRET ratio. Error bars represent s.e.m of duplicate wells from two separate experiments. The curve was fit to data (% TR-FRET vs. log IPA concentration) using a sigmoidal dose response (variable slope) equation in GraphPad Software.

Oral Dosing of IPA.

Pxr$^{+/+}$ and Pxr$^{-/-}$ mice were gavaged with 10, 20 and 40 mg/kg IPA, dissolved in sterile PBS (pH 7.4) in 100 µl volume per mice for four consecutive days. SW and SWGF mice were orally gavaged with 20 mg/kg IPA for four consecutive days.

Ex Vivo Treatment of Gut Apical Enterocytes with OLA.

Freshly isolated gut mucosa were incubated in the presence of OLA (5 mg/ml) for 3 h at 37° C., 5% CO2 (13). After 3 h of OLA treatment, enterocytes were isolated and pooled for RNA isolation. For rescue experiments, gut mucosa were incubated in the presence of indole (1 mM), IPA (1 µM) and OLA (5 mg/ml) for 3 h duration and subsequently enterocytes were isolated and pooled for RNA isolation. The short duration of exposure (3 h) required to minimize tissue degradation ex vivo necessitated use of supraphysiological concentrations of IPA. Experiments were performed at least two independent times. OLA has excellent drug-like properties with high predicted oral bioavailability (log P), thus is unsuitable for in vivo studies of luminal bacterial enzyme inhibition (Pubchem, ST093573).

Transmission Electron Microscopy.

Jejunum from mice were removed and 1 mm thick tissue slices were placed in ice cold 4% paraformaldehyde in 0.1 M phosphate buffer, pH 7.4, for 3 h with continuous shaking, after which slices were rinsed in cold phosphate buffer. These sections were post-fixed in 1% osmium tetraoxide and embedded in epon (Polysciences). Ultrathin 50 nm sections were prepared with LKB ultramicrotome, stained with lead citrate, and examined under a Philips 300 electron microscope (FEI Co.). Twelve identical sections (mid jejunum) from each mouse strain were analyzed for TEM and seven out of twelve sections showed defective tight junctions in Pxr$^{-/-}$ mice, while none were observed in Pxr$^{+/+}$ mice. For quantitation of average microvillus length, microvilli from all twelve sections were counted.

Enzyme Activity Assay.

Apical enterocytes isolated from mouse jejunum were pooled and subsequently lysed with RIPA lysis buffer and diluted in 0.1 M carbonate-bicarbonate buffer, pH 10.0. Differentially diluted enterocyte homogenate were exposed to p-Nitrophenyl Phosphate (pNPP) Liquid Substrate System (Sigma). Spectrophotometric quantitation (O.D. 405 nm) of p-nitrophenol (hydrolyzed product of pNPP), was used to measure alkaline phosphatase activity as previously published (34). Disaccharidase activity of pooled jejunal apical enterocytes was assessed using modified glucose oxidase peroxidase enzyme system as previously published (35). In brief, the assay was done in 96-well microtiter plates and to each well 10 µl appropriately diluted enterocyte homogenate and 10 µl substrate buffer solution of a disaccharidase were added. The plates were incubated at 37° C. in humidified atmosphere for 1 h. After incubation, 300 µl of tris-glucose oxidase (TGO) reagent was added to each well and the plates were incubated further for 1 h. The plates were subsequently read at O.D. 414 nm using a microplate reader (SpectraMaxR M5, Molecular Devices). For each assay, eight reagent blanks (20 µl distilled water and 300 µl TGO reagent) and glucose standard series (0.01, 0.1, 0.5, 1, 2, 4, 8 and 10 µg glucose) were performed. To assay Dipeptidyl Peptidase IV enzyme (DPPIV) activity, pooled jejunal apical enterocyte homogenate (differentially diluted) were used as enzyme source. The enzyme activity was measured with glycylproline p-nitroanilide (GP-pNA, Santa Cruz Biotechnology, Catalog #sc-201156) as a substrate. Spectrophotometric quantitation at O.D. 405 nm was analyzed to measure DPPIV enzyme activity as previously published (36). Experiments were performed at least two independent times each in triplicates.

Tissue Myeloperoxidase (MPO) Activity Assay.

Neutrophil infiltration in tissues was quantified by measuring MPO activity in pooled jejunum enterocyte homogenates as described previously (37). In brief, 50 mg of freshly isolated jejunum enterocytes were pooled and subsequently homogenized in 50 mM phosphate buffer and 0.5% hexadecyltrimethyl-ammonium bromide buffer (Sigma). The mixture was subjected to three cycles of freeze-thawing, followed by sonication for 20 seconds and centrifugation at full speed for 30 minutes. MPO activity was measured by incubating the supernatants with 20 mg/ml 0-dianisidine hydrochloride (Sigma) and 20 mM hydrogen peroxide. The reaction was terminated by adding 2% sodium azide. Optical density was read at 450 nm. Experiments were performed at least two independent times each in triplicates and are expressed as units per gram of tissue.

In Vivo Gut Permeability Assay.

Age and sex-matched mice were orally administered with 0.6 mg/g body weight of an 80 mg/ml solution of FITC-dextran (FD4, Sigma). 5 h later, retro-orbital blood was collected from each mouse. Serum was prepared by allowing the blood to clot by leaving it undisturbed overnight at 4° C. and then subsequently centrifuged at 3000 rpm for 20 minutes. Dilutions of FITC-dextran in PBS were used as a standard curve. Absorption of 50 µl serum was measured at microplate reader with excitation and emission filters set at 490 and 530 nm, respectively (38). Experiments were performed at least two independent times each in triplicates.

In Vivo Bacterial Translocation Assay.

pNEI-EGFP was transformed into E. coli JM 109 competent cells (Stratagene) and high-expression E. coli-EGFP clones were selected by fluorescence microscopy. Mice were gavaged with once daily dose of 1 ml E. coli-EGFP suspension (1×1011 cells/ml) for 3 consecutive days. 1 h after last feed, mice were sacrificed and jejunum harvested for fluorescence microscopy. Mice were fed with sterile drinking water containing ampicillin (300 mg/L) for 3 days prior to bacterial infection to facilitate the transformed E. coli to colonize their enteric lumen (39, 40).

Real-Time Quantitative RT-PCR.

2.0 µg of total RNA extracted from pooled apical enterocytes with TRIzolR (Invitrogen), were reverse transcribed with random hexamer primers and SuperScript™ III-RT enzyme (Invitrogen). Quantitative PCR (qPCR) reactions using TaqMan universal PCR master mix and TaqMan probes containing FAM as the 5' reporter fluorochrome and tetramethylrhodamine (MGB) as the 3' quencher fluorochrome, were performed in triplicate for each sample and analyzed on the ABI Prism 7900HT system. Primers and minor groove binder/non-fluorescent quencher probes used for PCR amplification were obtained from Applied Biosystems as well as the following assays on demand: Mm00500910_m1 (Occludin), Mm00493695_g1 (Zo-1), Mm01247357_m1 (E-cadherin), Mm00516703_s1 (Claudin-2), Mm00516817_m1 (Claudin-7), Mm00439616_m1 (Il-10), Mm01178819_m1 (Tgf-β), mB-Def3 (β-Defensin 3), mCryptdin4 (Cryptdin), Mm00458299_m1 (Mucin 2), Mm01612741_m1 (Lysozyme), Mm00438285_m1 (Cathelicidin), Mm00443258_m1 (Tnf-α), Mm01210733_m1 (Il-6), Mm99999071_m1 (Ifn-γ), Mm00441889_m1 (Tnfr-2), Mm00446095_m1 (Tlr1), Mm00442346_m1 (Tlr2), Mm00628112_m1 (Tlr3), Mm00445273_m1 (Tlr4), Mm00546288_s1 (Tlr5), Mm02529782_s1 (Tlr6), Mm00446590_m1 (Tlr7), Mm01157262_m1 (Tlr8), Mm00446193_m1 (Tlr9), Mm01701924_s1 (Tlr11), Mm00440732_g1 (Mdr-1), Mm99999915_g1 (Gapdh), Hs00152937_m1 (human TLR4), Hs01114265_g1 (human PXR), Hs02511055_s1 (UGT1A1), Hs00184500_m1 (hMDR-1), Hs00604506_m1 (CYP3A4) and Hu ACTB (β-actin). Controls include RT-minus RNA samples. PCR reaction conditions for all assays were set at 50° C. for 2 minutes, 95° C. for 10 minutes, followed by 40 cycles of amplification (95° C. for 15 seconds then 60° C. for 1 minute). Experiments were performed at least two independent times each in triplicates.

Immunoblot.

Freshly isolated jejunum apical enterocytes were pooled and subsequently lysed in RIPA lysis buffer containing 50 mM Tris (pH 7.5), 1% NP-40, 0.5% sodium deoxycholate, 0.05% SDS, 1 mM EDTA, 150 mM sodium chloride, protease inhibitors (Roche) and phosphates inhibitors (Sigma). 100 µg total lysates were heated to 95° C. for 5 minutes in 5×SDS sample buffer and loaded on 10% SDS-PAGE. Proteins were transferred to Nitrocellulose membranes (Bio-Rad laboratories). Membranes were stripped in western stripping buffer (Pierce) and reprobed sequentially with corresponding antibodies. Experiments were repeated at least two independent times each with three different exposure times.

Tandem Mass Spectrometry (LC/MS/MS).

IPA concentrations were analyzed in pooled plasma, intestinal tissue and feces by extraction and LC/MS/MS methods as previously published (14). In brief, samples were analyzed by ESCi multi-mode ionization (Waters TQ Tandem Quadrupole Mass Spec, Waters Corp.). The best ionization was achieved by positive ion electrospray. The MS/MS detection was developed and optimized using IntelliStart™ software. To demonstrate sensitivity, a linear calibration curve was created by serial dilutions of the stock standard (1-1000 ng/ml) in mouse plasma (data not shown, r2=99.9091×10-2). The lower limit of quantitation (LLQ)

for this assay is 5 picogram on the column with a signal to noise (S/N) ratio of 168.00. Tissue concentrations were established by normalizing to total protein content (Nano-Drop 1000 Spectrophotometer, Thermo Scientific) in cleared lysates (membrane-free) injected into columns.

Molecular Docking Studies.

Three dimensional structure of mPXR was modeled using the hPXR co-crystalized with hyperforin (PDB code: 1m13) as a template to the homology modeling program Modeller version 9.0 (41, 42). The resulting three dimensional structure was further refined via 1000 steps of conjugate gradient based energy minimization using Amber (version 9.0), with Amber charges as adopted in the Molecular Operating Environment (MOE) program (version 10; Chemical Computing Group, Montreal, Quebec, Canada). The binding site for mPXR was derived from hPXR-hyperforin complex and has been well characterized based on structural information derived from the variety of ligands that it binds to. Three dimensional models of IPA and indole were created using the Builder module of MOE and the structures were optimized using AM1 potentials. IPA structure was also subjected to stochastic conformational search adopted in MOE. The resulting conformations were clustered and a representative member from the highly populated, low energy ranking cluster was chosen for docking studies. To adequately sample this promiscuous binding site 50 independent docking runs were performed for each ligand and in combination to hPXR and mPXR using the GOLD program (Genetic Optimisation for Ligand Docking) (version 4.1) (43). The docked complexes were scored using Goldscore, Chemscore and a customizable scoring scheme that was previously designed to classify activators and non-activators of PXR (44-46). The best ranking complexes were then energy minimized using Amber force field adopted in MOE program.

In Vivo Toxic Gut Injury Models.

For indomethacin induced mouse jejunitis model, a protocol published by Ettarh and Carr was modified by using a single intraperitoneal dose of indomethacin to reduce the toxicity in Pxr$^{-/-}$ mice (17). In brief, mice were injected a single dose of indomethacin (85 mg/kg body weight) intraperitoneally and 48 h later mice were sacrificed and tissues harvested. For anti-CD3 antibody induced gut inflammation model, a previously published protocol (18) was followed. Briefly, mice were injected intraperitoneally with 200 anti-CD3 antibody (clone 2C11, BD biosciences) in 200 µl of PBS. 3 h later, mice were sacrificed and jejunum sections were carefully removed and tied at both ends with same length sutures. Weights of individual jejunum sections were measured for quantitation of enteropooling (intestinal weight/length in mg/cm). In the intestinal FR injury model, a previously published protocol (19) was followed. Briefly, mice were gavaged with 0.6 mg/g body weight of an 80 mg/ml solution of FITC-dextran (FD4, Sigma) and 15 minutes later anaesthetized by pentobarbital (50 mg/kg intraperitoneally). A laparotomy was performed, followed by occlusion of superior mesenteric artery with a microvascular clamp (BRI, Inc. Catalog #34-2805). After 20 minutes of ischemia, the clamp was removed and incision closed. Mice were allowed to recover from anesthesia and serum collected retro-orbitally following 3 h of reperfusion. In the low dose endotoxic shock model, mice were initially sensitized with an intraperitoneal injection of 40 mg D-galactosamine (Sigma) administered 15 minutes before an intravenous injection of 50 ng of *E. coli* ultra pure O111:B4 lipopolysaccharide (LPS) (Sigma) (20). A protocol was developed for gut mucosal endotoxemia model, where 200 µg of highly potent LPS substitute KDO2-lipid A (Catalog #699500P; Avanti Polar Lipids, Inc.) were delivered via sterile injection directly into mice jejunum. These mice were already pre-gavaged with 200 µl of 10% sodiumbicarbonate 15 minutes earlier to decrease gastric acidity. 24 h after the injection, mice undergo FITC-dextran gavage, mRNA expression analysis and necropsy studies.

Bone Marrow Transplantation.

Mice (6-8 week) receiving bone marrow transplantation were irradiated (600 RAD) on the morning of transplantation and 4-6 hours later, immediately before transplantation. Bone marrow were harvested from femurs and tibias of 6 week old Pxr$^{+/+}$ or Pxr$^{-/-}$ mice with RPMI (10% Fetal Calf Serum), and cell suspensions were washed and diluted to a concentration of 30×106 cells/ml in HBSS. 7.5×106 cells/250_l were injected intravenously into the lateral tail veins of the recipient mice. Transplanted mice were placed on antibiotic water (0.7 mM neomycin sulfate, 80 mM sulfamethaxazole and 0.37 mM trimethoprim) for 2 weeks after irradiation, and then given autoclaved water to reconstitute normal gut flora. Mice were kept for 6 weeks to ensure full engraftment and maturation of the immune system before experiments (47).

BrdU and TUNEL Staining.

Mice were injected with 1 mg bromodeoxyuridine (BrdU, Becton Dickinson) in 500 µl PBS. Small gut was harvested after 24 h and paraffin embedded tissues was stained with anti-BrdU antibody (Calbiochem, JA1599). TUNEL staining in paraffin embedded small gut sections was performed in the Histology core facility of Albert Einstein College of Medicine.

TLR2 and 4 Inhibition Experiments.

Freshly isolated jejunum apical enterocytes were incubated in the presence of TLR2 inhibitory antibody (50 µg/ml, eBioscience, 14-9024-82) and TLR4 inhibitor (100 µg/ml, Invivogen, lps-rs) for 3 h at 37° C., 5% CO2. After incubation, enterocytes were isolated and pooled for RNA isolation. Experiments were repeated at least twice.

Lenti-Based shRNA Knock-Down Systems.

For PXR shRNA lentiviral plasmid design and construction, a protocol published by Sun et al. (48) was used. Details of the procedure can be found in a recent publication (49).

Actinomycin D Chase Experiment.

LS174T cells were plated into 6 well tissue culture dishes and treated with rifampicin for 48 h. After rifampicin treatment, 20 µg/ml of Actinomycin D, dissolved in DMSO was added in each well and RNA isolated at different time points starting at t=0 after Actinomycin D exposure. RNA was subsequently used for reverse transcription and real-time qPCR analysis.

RNA Immunoprecipitation Assay.

293T cells, transfected with PXR expression vector and TLR4 3'UTR construct, were formaldehyde (1%) cross-linked prior to lysis. Cell lysates was prepared in RIPA buffer containing protease inhibitor and RNasin (Promega, catalog #N251A). Cell lysates were sonicated for three cycles (20 seconds each, amplitude 7, duty cycle 70%, output 8-9W). Pre-clearing steps by incubating cell lysates with protein A-agarose beads were performed to minimize non-specific binding. Pre-cleared cell lysates was incubated with antibody coated beads (protein A-agarose incubated with 10 µg each of PXR and IgG antibody for 2 h at 4° C.) subsequently at 4° C. overnight. Next morning, beads were washed five times in RIPA buffer containing RNasin and resuspended in resuspension buffer (50 mM Tris-HCl, 5 mM EDTA, 10 mM DTT and 1% SDS) at 70° C. for 45 min to reverse the cross-link. RNA was extracted from the beads with TRIzol Reagent, ethanol-precipitated, and resuspended in 20 µl RNase-free water. RNA solution prepared was further treated with TURBO DNase (Invitrogen, catalog #AM2238) to get rid of any contaminating DNA. This RNA solution was used for semiquantitative PCR.

Isolation of Nuclei and Nuclear Run-on Assay.

These assays were performed according to the methods previously published with minor modifications to allow for small scale RNA synthesis (50). For nuclear isolation, LS174T cells cultured in 10 cm dishes were digested with 5 ml volume of 0.25% trypsin/0.1% EDTA. The cells were centrifuged at 500 g for 10 min. The cells were resuspended in Buffer 1 (containing 10 mM Tris-HCl, pH 7.4/150 mM KCl/8 mM magnesium acetate) and centrifuged at 500 g for 10 min. Pellets were then resuspended and lysed in Buffer 1 with addition of 0.5% Nonidet P-40 on ice for 5 min. The lysates were set onto Buffer 2, which contained 100 mM Tris-HCl, 5 mM MgCl2 and 600 mM sucrose, and centrifuged at 500 g for 10 min. The pellets (nuclei) were then resuspended in Buffer 3 containing 40% glycerol, 50 mM Tris-HCl, 5 mM MCl2 and 0.1 mM EDTA. Nuclei were immediately stored at −80° C. in Buffer 3, until nuclear run-on transcription assay. For nuclear run-on assay, identical number of LS174T nuclei was used for preparation of nascent transcripts. To perform the nuclear run-on transcription, 5×106 nuclei were incubated in a reaction buffer (5 mM Tris-HCl, pH 8.0, 2.5 Mm MgCl2, 150 mM KCl, 1.0 mM each of ATP, GTP, CTP) and 0.5 mM biotin-16-UTP at 30° C. for 45 min in a final volume of 25 µl. The reaction was stopped by the addition of 60 U RNase-free DNase and incubated further for 10 min at 37° C. The nuclei were then lysed by the addition of lysis buffer containing 10 Mm Tris-HCl, 1% SDS, 5 mM EDTA. The reaction mixtures were treated with 20 µl of proteinase K (10 mg/ml). RNA was extracted with TRIzol Reagent, ethanol-precipitated, and resuspended in 50 µl RNase-free water. Biotinylated RNA was purified by adding streptavidin beads, followed by 2 h incubation at 25° C. on a shaker. Beads were separated by centrifugation at 2,000 rpm for 5 min, and washed once with 2×SSC-15% formamide for 10 min and twice with 2×SSC alone for 5 min. Finally, beads were resuspended in 30 µl DEPC treated water. The biotinylated RNA solution was used for reverse-transcriptase cDNA synthesis and further real-time qPCR for the quantitative mRNA assay.

Chromatin Immunoprecipitation (ChIP) Assay.

A fast ChIP method was used as previously published (51). In fast ChIP method, LS174T cells were cross-linked with formaldehyde, following which the cells were lysed and fractions containing nuclear pellets isolated and chromatin sheared. The sheared chromatin samples were subsequently incubated with respective antibodies in an ultrasonic bath, followed by centrifugation to obtain pre-cleared samples. Precleared samples were then mixed with protein A agarose beads. After several washes, Chelex 100 suspension was added to the beads, the suspension boiled and tubes were allowed to cool. After shaking and repeated boiling, the centrifuged samples were analyzed for PCR-ready DNA. A 30 cycle PCR was used to detect interaction. The input reflects 0.5% of total lysate after sonication. Immunoprecipitation controls included $H_2O$ (water) and non-specific IgG (same class as PXR antibody). The primers used for PXR binding site within the TLR4 promoter were as follows.

For proximal binding site (amplicon size is 320 bp):

```
Forward:
                                   (SEQ ID NO: 8)
5'-CAGTCTCTTCCCAGATGC-3'
and Reverse:
                                   (SEQ ID NO: 9)
5'-GTGAGGGACCATTTTGTG-3'.
```

For distal binding site (amplicon size is 381 bp):

```
Forward:
                                   (SEQ ID NO: 10)
5'-GGACTGGTAATGGGTGTC-3'
and Reverse:
                                   (SEQ ID NO: 11)
5'-CCATCCAACCATCTCAAG-3'.
```

The positive control in this assay was PXR binding site within the CYP3A4 promoter (ER3 elements 188 bp amplicon):

```
Forward:
                                   (SEQ ID NO: 12)
5'-GAGGTGTCACTGCCATCTTCAT-3'
and Reverse:
                                   (SEQ ID NO: 13)
5'-GAGGCTGCTTACTCTGGGTTTT-3'.
```

TLR4 3'UTR Luciferase Construct.

TLR4 mRNA 3'UTR region was PCR amplified with the following primers:

```
forward:
                                   (SEQ ID NO: 14)
5'-GATCTCTAGAAAGAAGGAACAGTGGGTAC-3'
and reverse:
                                   (SEQ ID NO: 15)
5'-GATCTCTAGAACTTTCCCAGGTTTCATGG-3'.
```

For TLR4 3' UTR luciferase reporters, PCR products were digested with Xba I restriction enzyme (New England Biolabs) and cloned into Xba I site, downstream of luciferase reporter of pGL4.13 vector. Luciferase assay was performed similar to the transcription assays as previously mentioned.

Statistical Analysis.

Data are shown as means±s.e.m. The significance of difference was analyzed by two-tailed Student's t-test or ANOVA with post-hoc Bonferroni test. The Kaplan-Meier method was used for survival and differences was analyzed by the log rank test. All analyses were performed using GraphPad PRISM version 5.03 (GraphPad Software). P<0.05 was considered statistically significant.

Results and Discussion

Figures 5A, 5B:
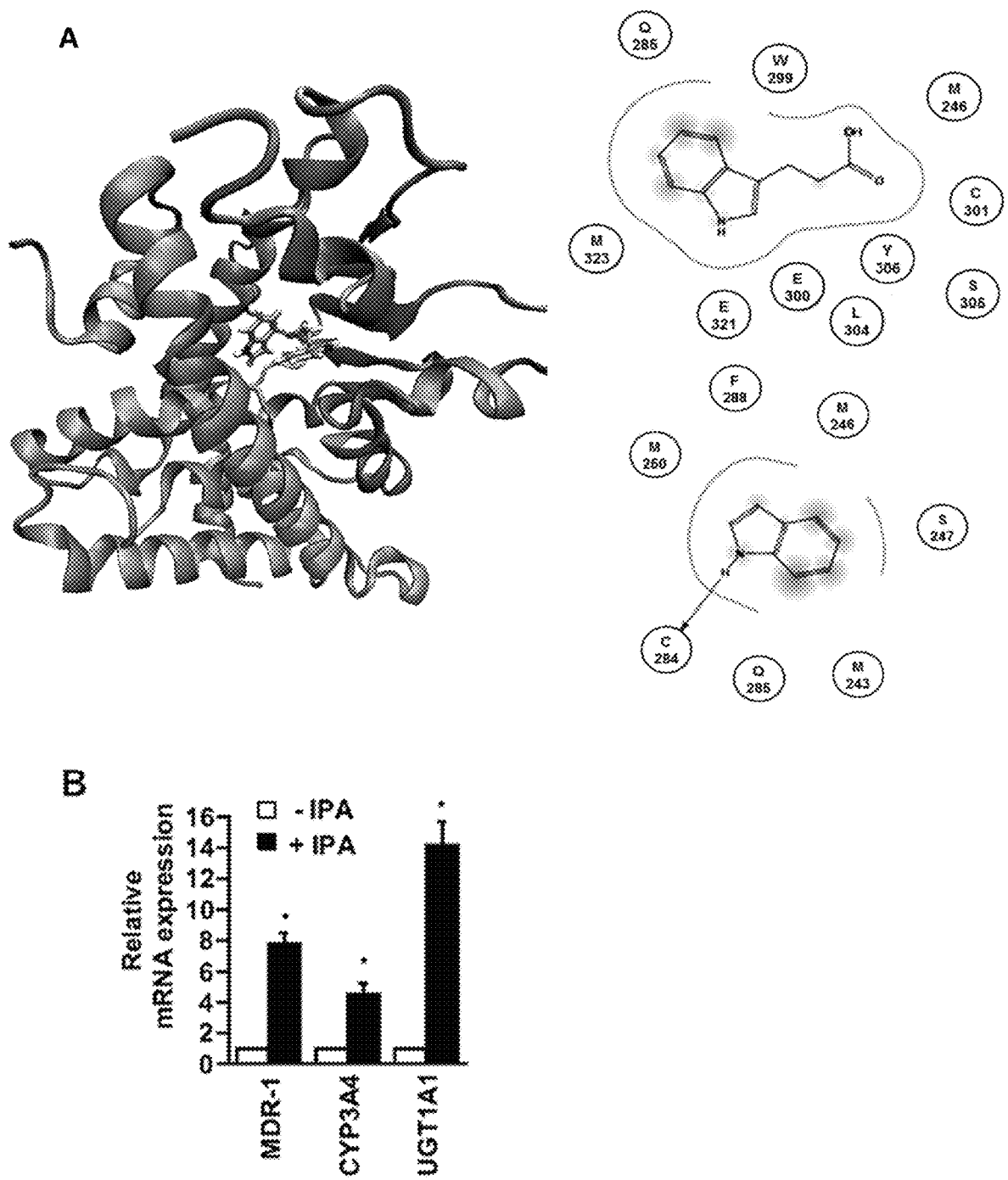
FIG. 5A-5K. IPA shows PXR agonistic activity. (A) Molecular docking result for indole and IPA is shown. Indole and IPA in licorice representations were docked to the binding site of hPXR shown in cartoon representation and colored orange (left). Schematic representation of molecular interactions of indole and IPA in hPXR is shown in right. The 2D schematic diagrams shown in right were generated using the LIGX module of MOE program. The binding site residues are colored by their nature, with charged residues highlighted with bold contours. Results from docking studies show that concurrent binding of indole and IPA was preferred over individual binding of either ligand as they occupied a larger binding pocket with favorable interactions. Concurrent binding scores were also comparable to the docking scores produced by strong PXR binders such as rifampicin. (B) Real-time qPCR analysis of MDR-1, CYP3A4 and UGT1A1 mRNA expression in differentiated Caco-2 cells co-treated with indole (1 mM) and IPA (1 µM). (C) Serum FITCdextran permeability assay in Pxr+/+, hPXR and Pxr−/− mice (n=5 mice per group). (D) Transcriptional activity of luciferase target reporter genes (Tk-MRP2 luciferase, Tk-MH100 luciferase and CYP2B6 luciferase) co-transfected with human PXR, GAL4-FXR, FAL4-LXR, GAL4-PPARγ, mouse CAR expression plasmids in 293T cells following treatment with fixed concentration of indole (1 mM) and IPA (1 µM) (n=3). RLU, relative light unit. Data expressed as fold change in RLU compared to vehicle (DMSO) controls. ***P≤0.001 (ANOVA with Bonferroni test). (E) Hematoxylin and eosin staining of jejunum cross-sections from Pxr+/+ and Pxr−/− mice treated with KDO2 (200 µg/mice) shows no histologic evidence of overt inflammation in either group. (F) Real-time qPCR analysis of Pxr+/+ mice treated with $KDO_2$ (dose: 10, 100 and 200 µg/mice) shows dose-dependent increase in Tnf-α mRNA expression (n=6 mice per group). (G) Immunoblot analysis of jejunal apical enterocyte from Pxr+/+ mice treated with $KDO_2$ (dose: 10, 100 and 200 µg/mice) shows dose-dependent increase in phosphop38-MAPK protein levels (n=6 mice per group). (H) In vivo FITC-dextran permeability assay in Pxr+/+ mice treated with $KDO_2$ (200 µg/mice) (n=6 per group). (I) IPA concentrations were measured in blood, intestinal tissue and feces in Pxr+/+ mice, orally gavaged with 20 mg/kg IPA by tandem mass spectrometry. (J) SW (control) and SWGF mice were orally gavaged with IPA (20 mg/kg) for four consecutive days and FITC-dextran permeability assay was performed (n=3 mice per group). (K) IPA concentrations were measured in intestinal tissues by tandem mass spectrometry after ex vivo treatment of Pxr+/+ mice intestine with OLA, indole and IPA. All graphs show mean values±s.e.m. *P≤0.05; P≤0.01; *P≤0.001. Scale bars, 50 μm.
Figures 5C, 5D, 5E, 5F, 5G, 5H, 5I, 5J, 5K:
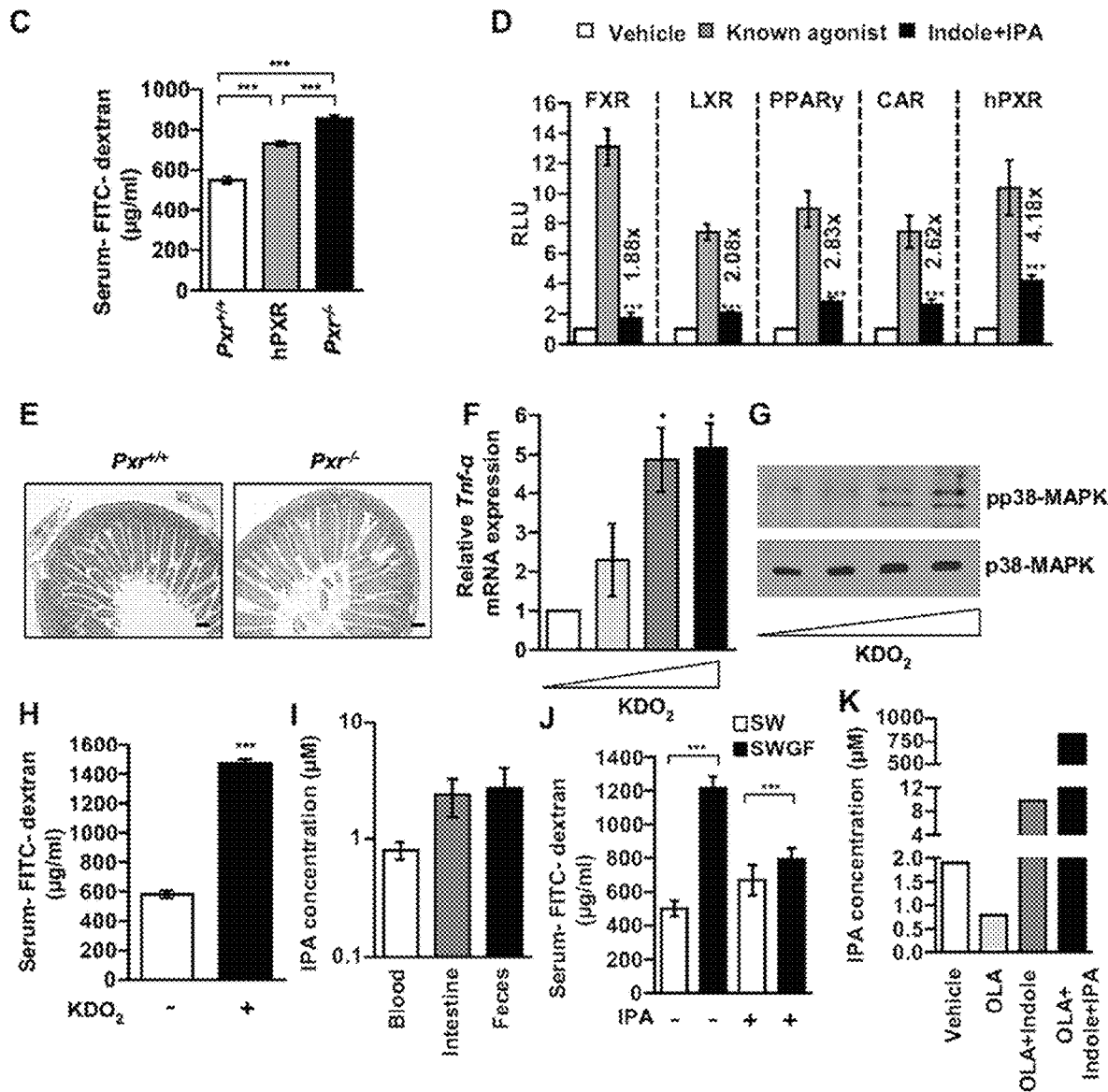

To simulate in vivo homeostatic conditions, PXR transcription assays were conducted using a combination of indole with its respective metabolites. While IPA alone is a weak human PXR (hPXR) agonist ($EC_{50}$ 120 µM, Emax 6.38 fold over control); IPA [including indoxyl sulphate (I3 S), indole acetic acid (IAA)] in combination with indole significantly activates hPXR (FIG. 1A, B to D). In silico docking studies support these findings (FIG. 5A). By contrast, mouse PXR (mPXR) is potently activated by IPA (EC50 0.55 µM, Emax 18.84 fold over control) in vitro and induces PXR target gene transcription in vivo (FIG. 1A, E and FIG. 5B). Indeed, the differences in PXR potency of indoles was also evident on in vivo epithelial permeability assay, where humanized PXR transgenic mice (hPXR) are more permeable to FITC-dextran when compared to $Pxr^{+/+}$ mice (FIG. 5C). In silico docking studies suggest that both an indole and IPA can be accommodated simultaneously in the PXR ligand binding pocket (Table 1). LanthaScreen time-resolved fluorescence resonance energy transfer (TR-FRET) PXR competitive binding assay shows IPA had EC50 for ligand displacement in mPXR and hPXR of 1.1 µM and 2.1 µM, respectively (FIG. 1F). The apparent discrepancy between EC50 differences in transcription versus ligand-binding assays has been observed with small hydrophobic PXR ligands (9). The combination of indole and IPA also activated other orphan nuclear receptors that play a role in gut barrier protection (e.g., farnesoid x receptor), suggesting a crucial role of indoles in maintaining gut barrier function involving multiple nuclear receptors (FIG. 5D) (10). However, hPXR activation was greater in comparison to other nuclear receptors tested (FIG. 5D).

The effect of indoles on enterocyte inflammatory signals and barrier function was examined in an in vivo model of 3-deoxy-D-manno-octulosonic acid (KDO2)-lipid A intubation, which elicits inflammatory signals without disrupting the intestinal tissue architecture (see Methods). Because TNF-α plays a critical role in barrier dysfunction, it was used as marker of gut barrier dysfunction (11). There was no overt histologic evidence of inflammation; however, TNF-α, MAPK phosphorylation and permeability to FITC-dextran were clearly induced after KDO2 treatment (FIG. 5E to H). In this model, at IPA concentrations that are achievable through oral gavage, IPA notably decreases Tnf-α mRNA expression more in the $Pxr^{+/+}$ mice gut epithelium relative to $Pxr^{-/-}$ mice (FIG. 1G and FIG. 5I).

Indoles are produced in the gut from L-tryptophan by the action of bacterial tryptophanase enzyme (6). IPA repletion in germ free mice decreased gut permeability to FITC-dextran (FIG. 5J). Oxindolyl L-alanine (OLA), a potent tryptophanase inhibitor, blocks production of indoles and its metabolites in the gut (12, 13). To determine the effect of indole and IPA on key parameters of gut barrier function, $Pxr^{+/+}$, $Pxr^{-/-}$ and hPXR mice gut epithelium were exposed to OLA ex vivo. IPA concentrations were analyzed in intestinal tissues using tandem mass spectrometry based methods (FIG. 5K) (14). Blocking indole and IPA production in all mice genotypes resulted in enhanced enterocyte Tnf-α mRNA expression and diminished expression of junctional regulators (Zo-1 and E-cad), consistent with its prior role as an anti-inflammatory mediator (FIG. 1H) (8). Ex vivo rescue of indole and IPA depletion resulted in significant reduction in Tnf-α and increase in Zo-1 and E-cad mRNA expression (FIG. 1H). Importantly, these effects were absent in $Pxr^{-/-}$ mice, thus establishing PXR as an important enterocyte target of IPA (FIG. 1H).

Figures 2A, 2B, 2C, 2D, 2E, 2F, 2G, 2H, 2I:
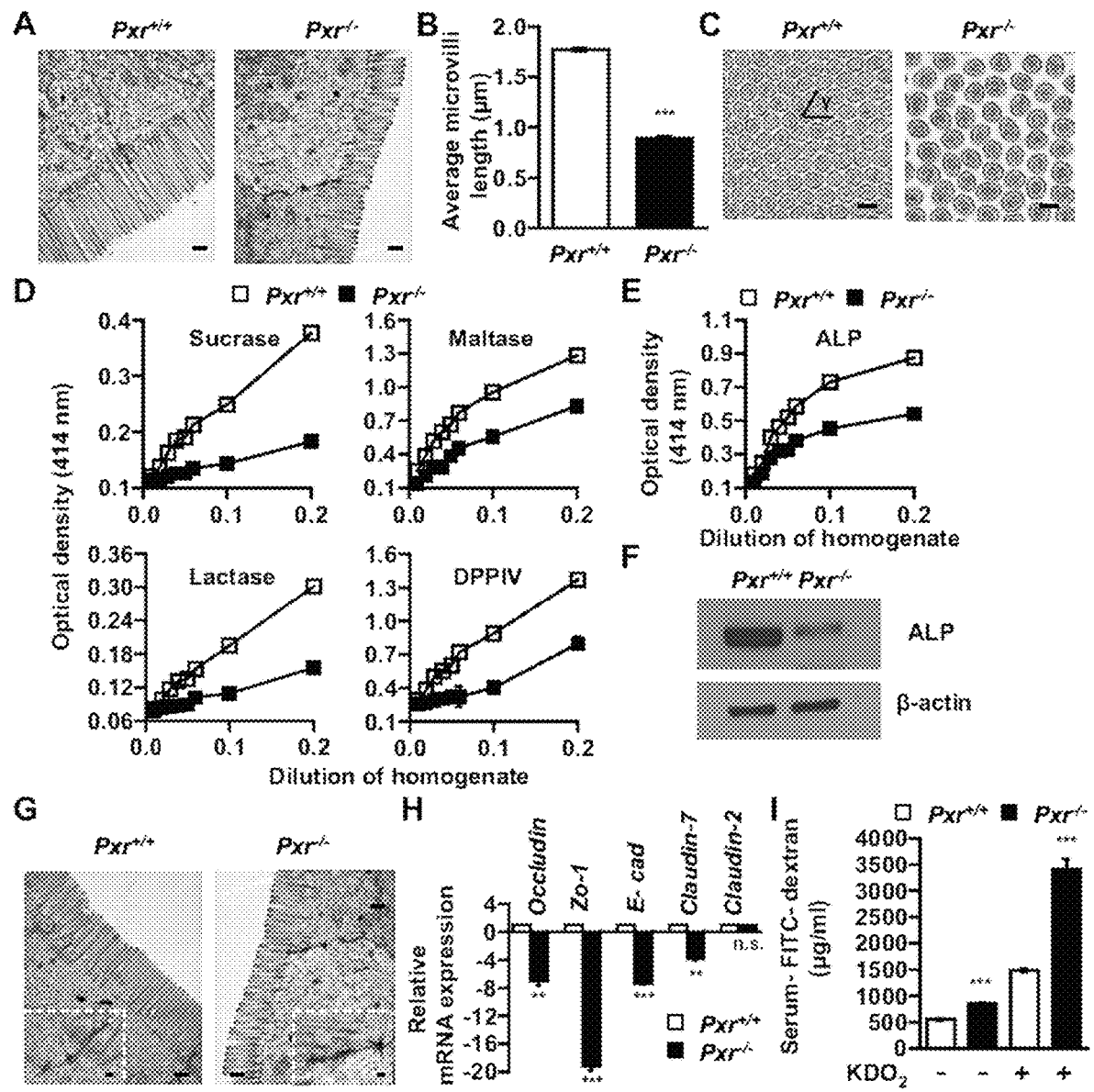
FIG. 2A-2I. Ultra-structural and functional defects in Pxr−/− mice gut. (A) Representative TEM images of Pxr$^{+/+}$ and Pxr−/− mice jejunum reveals shorter microvilli in Pxr−/− mice. (B) Graph showing average microvillus length in Pxr−/− mice jejunum (0.89 µm) is 50.3% shorter compared to Pxr$^{+/+}$ mice (1.77 µm) (n=5 mice per group). (C) Representative TEM images of Pxr$^{+/+}$ and Pxr−/− mice jejunum shows loose packing of microvilli in Pxr−/− mice. γ represents packing angle between adjacent microvilli. (D) Sucrase, maltase, lactase and dipeptidyl peptidase (DPPIV) enzyme activities were determined from Pxr$^{+/+}$ and Pxr−/− mice jejunum apical enterocytes. Proportionality between amount of enzyme present (jejunal apical enterocyte homogenate containing 20 mg/ml of protein as enzyme, x-axis) and amount of substrate liberated (optical density, y-axis) in 60 minutes was plotted in the graph. Pxr−/− mice reveals significantly diminished enzyme activities when compared to Pxr$^{+/+}$ mice (n=8-10 mice per group). (E) Diminished alkaline phosphatase enzyme activity in Pxr−/− mice jejunum apical enterocyte homogenate than those in the Pxr$^{+/+}$ mice (n=8-10 mice per group). (F) Immunoblot analysis for alkaline phosphatase and β-actin (loading control) in Pxr+/+ and Pxr−/− mice jejunum apical enterocytes (n=5 mice per group). (G) Representative TEM images of Pxr+/+ and Pxr−/− mice jejunum demonstrate disruption of cell-cell junctional complexes and marked perijunctional cytoskeletal condensation in Pxr−/− mice. Inset shows magnified views of cell-cell junctional complex. (H) Real-time qPCR analysis of key Tj and Aj regulatory genes in Pxr+/+ and Pxr−/− mice jejunum apical enterocytes (n=8-10 mice per group). Data plotted as fold change in Pxr−/− mice relative to mRNA levels in Pxr+/+ mice. (I) Serum FITC-dextran permeability assay in Pxr+/+ and Pxr−/− mice following treatment with $KDO_2$. (n=8-10 per group). All graphs show mean values±s.e.m. *P≤0.05; P≤0.01; *P≤0.001, n.s. not significant. Scale bars: A, C and G, 0.5 µm.
Figures 6A, 6B:
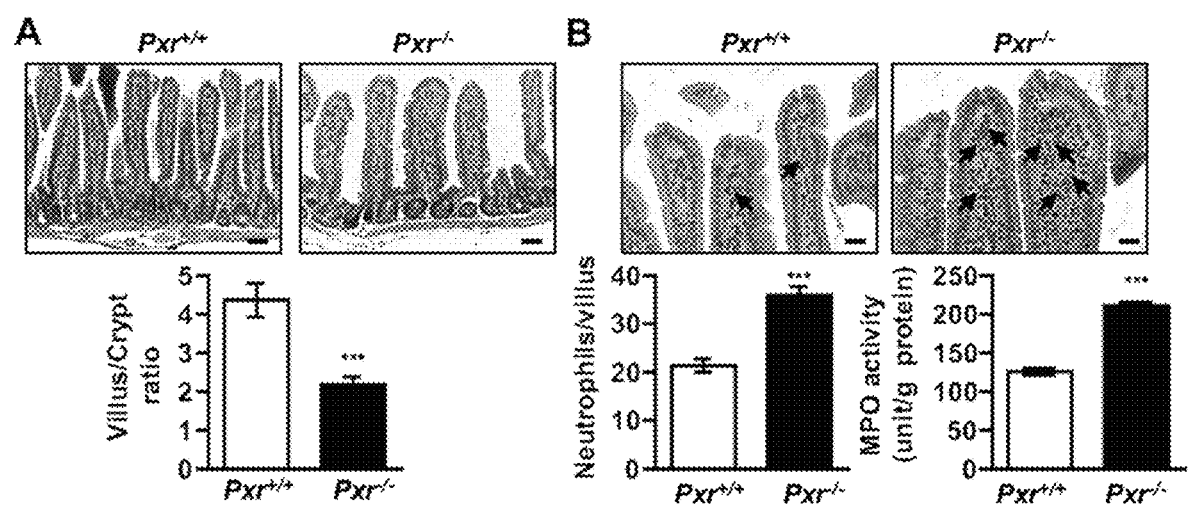
FIG. 6A-6B. Histopathology of Pxr−/− mice small gut. (A) Representative pictures of hematoxylin and eosin stained Pxr+/+ and Pxr−/− mice jejunum cross-sections (top) and assessment of villus: crypt ratio (bottom) shows diminished villus:crypt ratio in Pxr−/− mice (n=5 mice per group). (B) Hematoxylin and eosin staining of Pxr+/+ and Pxr−/− mice jejunum cross-sections showing increased number of neutrophils present in lamina propria of Pxr−/− mice jejunum (arrows indicate individual neutrophils) (top). Neutrophils were quantified by counting in 10 randomly chosen villi from five mice in each group (bottom left). MPO activity assay was performed in jejunal enterocyte homogenates (n=8-10 mice per group) (bottom right). All graphs show mean values±s.e.m. ***P≤0.001. Scale bars, 50 μm.
Figures 7A, 7B, 7C, 7D, 7E, 7F, 7G:
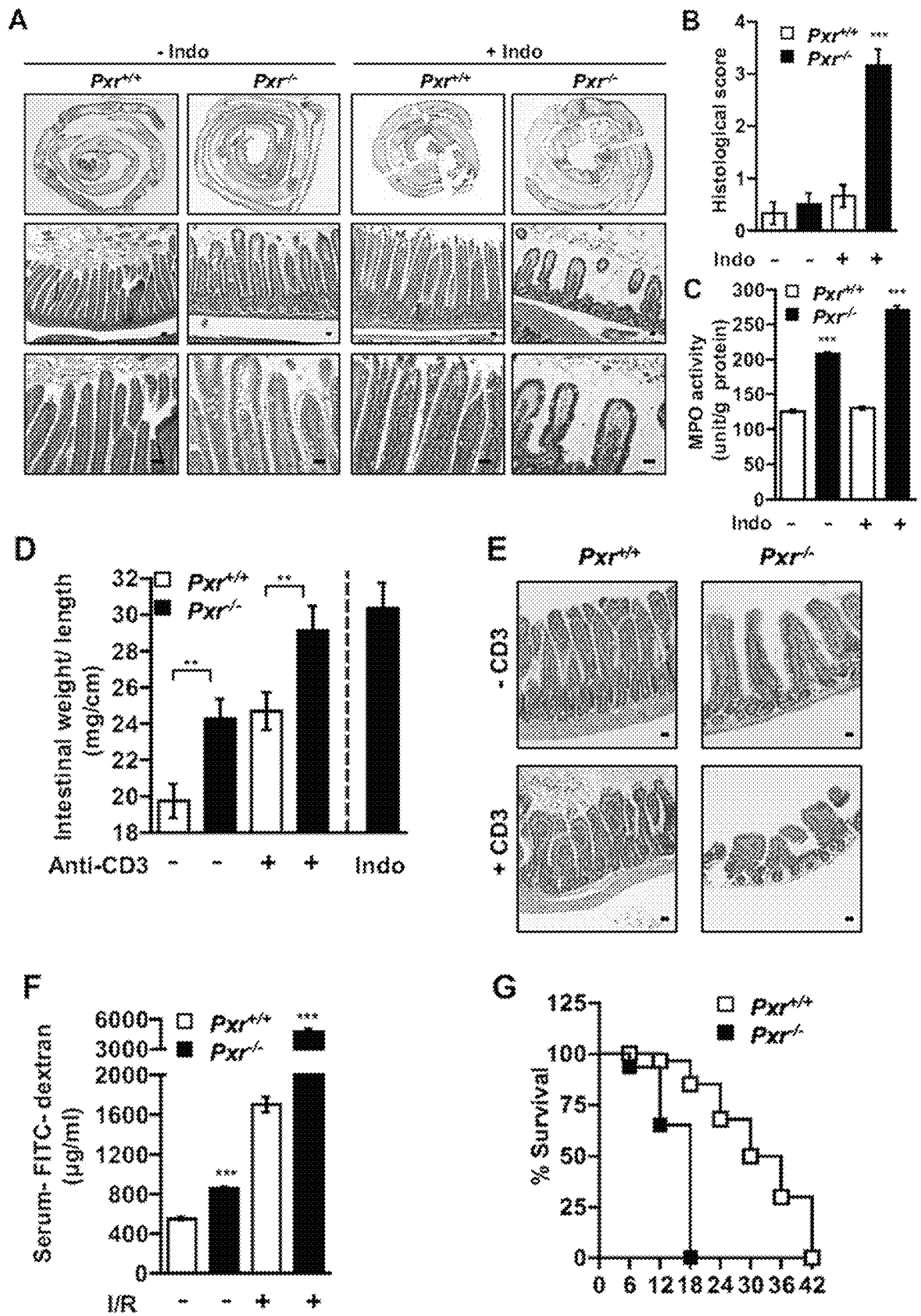
FIG. 7A-7G. Pxr−/− mice are more susceptible to toxic injuries to the gut. (A) Hematoxylin and eosin staining of indomethacin (Indo) treated Pxr+/+ and Pxr−/− mice jejunum cross-sections showing increased epithelial erosions and villi damage in Pxr−/− mice jejunum. (B) Histological score measuring severity of tissue damage in jejunum from Pxr+/+ and Pxr−/− mice in indomethacin treated and untreated groups (n=6 mice per group). (C) Jejunal MPO activity (Unit/g of protein) was determined in Pxr+/+ and Pxr−/− mice treated with indomethacin (n=6 per group). (D) Weight to length ratio of the jejunum (enteropooling), an indicator of edema and fluid accumulation, was determined in Pxr+/+ and Pxr−/− mice treated with anti-CD3 antibody for 3 h. The change in weight-to-length ratio in Pxr+/+ and Pxr−/− mice exposed to anti-CD3 was 27.6% and 22.9%, respectively. Note that, while the changes in weight-to-length ratios in Pxr+/+ and Pxr−/− mice are not significantly different from their respective baseline, it is clear that the Pxr−/− mice have increased susceptibility to anti-CD3 mediated injury. Furthermore, mean weight-to-length ratios (~29.5 mg/cm) approximate saturated values observed with indomethacin (~30 mg/cm) in Pxr−/− mice. Values represent mean±s.e.m. (n=5 mice per group). (E) Hematoxylin and eosin staining of anti-CD3 antibody treated Pxr+/+ and Pxr−/− mice jejunum cross-sections shows gross villi damage in Pxr−/− mice jejunum. (F) Epithelial permeability following gastrointestinal ischemia-reperfusion (FR) injury was assessed by FITC-dextran in Pxr+/+ and Pxr−/− mice exposed to 20 minutes of ischemia followed by 3 h of reperfusion. Serum is collected following reperfusion and FITC levels assayed (n=5 mice per group). The change in permeability as assessed by a change in recovery of mean levels of FITC-dextran in the serum of Pxr+/+ and Pxr−/− mice was 193% and 488.9%, respectively. (G) Kaplan-Meier survival curves of Pxr+/+ and Pxr−/− mice treated with LPS (n=6 per group). Pxr−/− mice treated with LPS had significantly worse survival than its Pxr+/+ counterpart. All graphs show mean values±s.e.m. *P≤0.05; P≤0.01; *P≤0.001. Scale bars, 50 μm.
Figure 8:
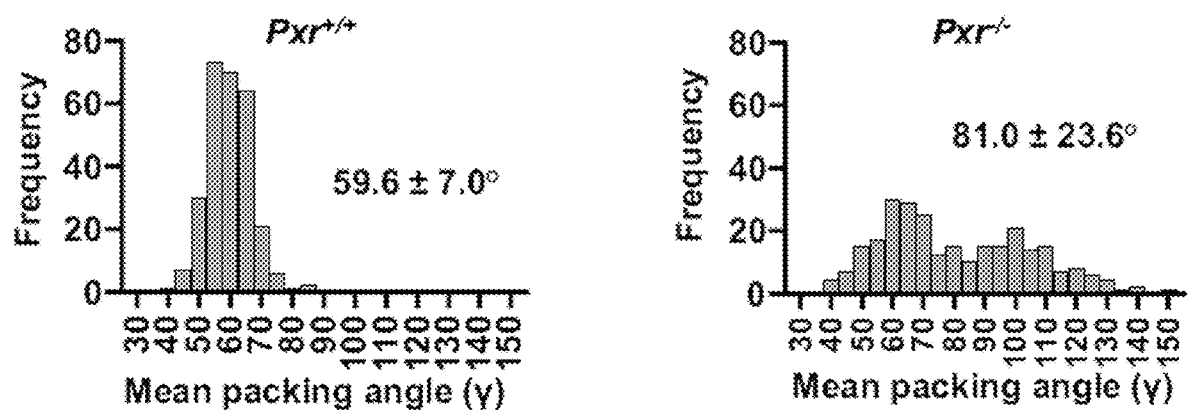
FIG. 8. Ultra-structural and functional changes in Pxr−/− mice gut. (A) Packing of microvilli in Pxr+/+ and Pxr−/− mice jejunum was quantified by assessing the packing angle (γ) between adjacent microvilli. γ in Pxr−/− mice cross-sections (81.0±23.6°, n=273) is significantly higher and more variable compared to Pxr+/+ mice (59.6±7.0°, n=275) (n=5 mice per group).

To study the function of PXR under steady-state conditions, detailed histological analysis was performed using 6-8 week old $Pxr^{-/-}$ and $Pxr^{+/+}$ mouse intestines. While gross features appeared unchanged, histological examination of the mucosa of $Pxr^{-/-}$ mice small intestines showed significant diminution of the villus-crypt ratio, marked neutrophil infiltration and increased myeloperoxidase (MPO) enzyme activity (FIGS. 6A and 6B). The data shown compare the jejunum (highest expression of PXR in the gut) of wild-type ($Pxr^{+/+}$) and $Pxr^{-/-}$ mice; data pertaining to other regions (i.e. duodenum, ileum) have similar trends (data not shown) (15). By contrast, these histological differences between $Pxr^{-/-}$ mice and $Pxr^{+/+}$ mice were not observed in the colon (data not shown) as noted previously (15, 16). While subtle, these differences indicate that the small gut of $Pxr^{-/-}$ mice may persist in a state of elevated stress that may culminate as overt inflammation when exposed to injurious insults. To investigate whether PXR deficiency sensitizes mice to toxic insults, $Pxr^{-/-}$ and $Pxr^{+/+}$ mice were subjected to four toxic gut injury models. In Pxr deficient mice, all four direct and indirect gut injury models show clear evidence for heightened sensitivity towards toxic injury (FIG. 7) (15, 17-21). The lack of steady-state gross inflammatory pathology in $Pxr^{-/-}$ mice, though, sharply contrasts this heightened sensitivity towards xenotoxic challenge. To reconcile these findings, ultra-structural and biochemical analysis of $Pxr^{+/+}$ and $Pxr^{-/-}$ mice jejunal epithelium were performed. Transmission electron microscopy (TEM) of $Pxr^{-/-}$ mice intestinal epithelial cells showed loosely packed shorter microvilli relative to $Pxr^{+/+}$ mice (FIG. 2, A to C and FIG. 8). Additionally, $Pxr^{-/-}$ mice microvilli show significantly diminished digestive enzyme activities compared to $Pxr^{+/+}$ microvilli, and the amount and activity of alkaline phosphatase is also notably reduced in the $Pxr^{-/-}$ mice gut (FIG. 2, D to F). Together, these data demonstrate that key aspects of the fine structure and enzyme expression in the $Pxr^{-/-}$ mice gut would explain its sensitivity towards xenobiotic challenge. The cell-cell junctional complex, an essential structural component of the epithelial barrier, was examined. TEM showed that the tight-junction (Tj) and adherens-junction (Aj) complex in $Pxr^{-/-}$ mice gut epithelium to be significantly more electron dense, diffuse with dense interconnected stranding (FIG. 2G). The mRNA expression of these key junctional-complex markers were markedly diminished in the $Pxr^{-/-}$ mice, except Claudin-2 which is known to induce barrier defects (FIG. 2H) (22). Immunofluorescence showed similar trends. Furthermore, in comparison with $Pxr^{+/+}$ mice, there is increased FITC-dextran recovery and presence of GFP-labeled E. coli in serum and lamina propria, respectively, of $Pxr^{-/-}$ mice (FIG. 2I). Together, these ultra-structural and functional assays implicate PXR as a physiologic regulator of gut barrier function.

Figures 3A, 3B, 3C, 3D, 3E, 3F, 3G, 3H:
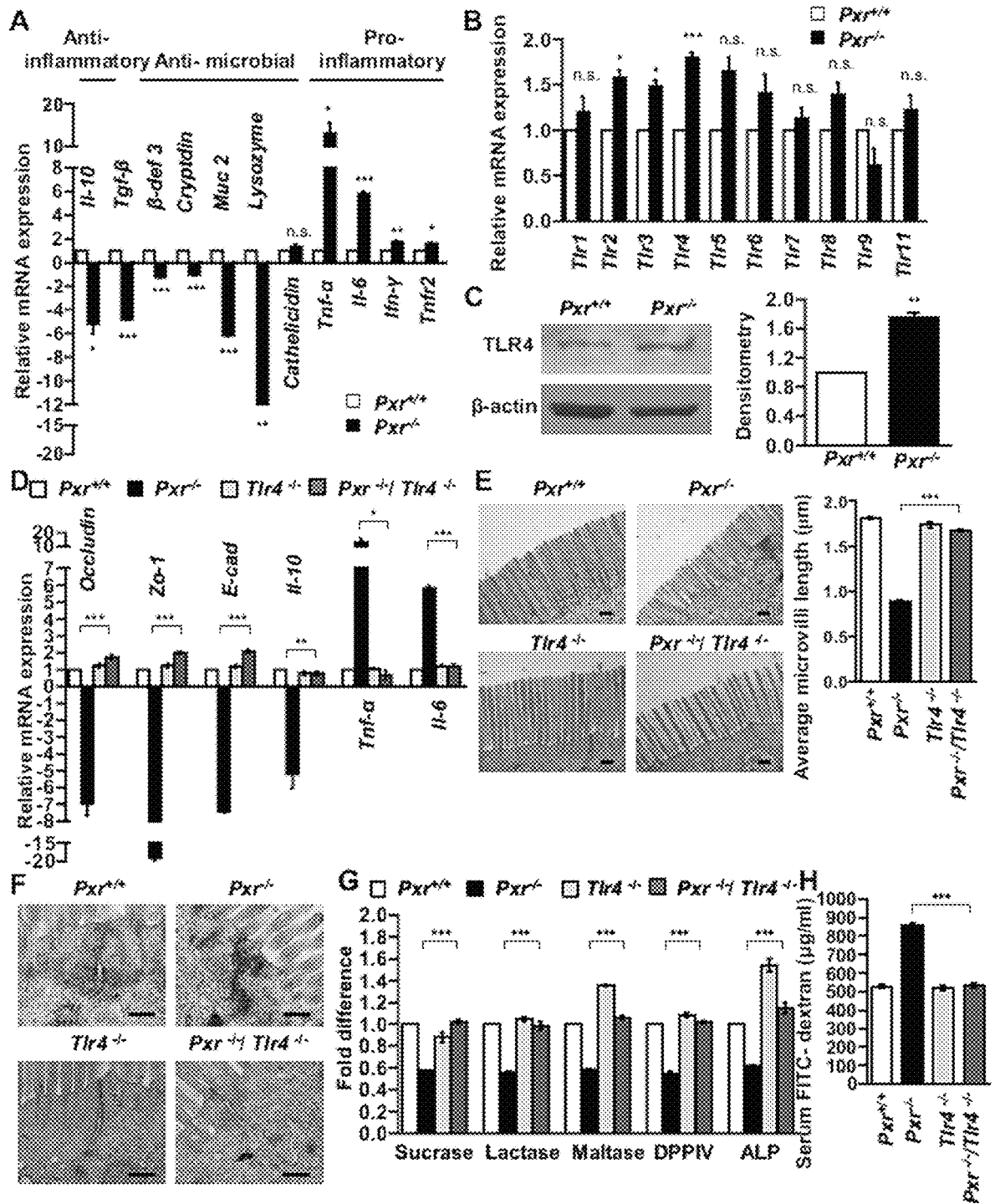
FIG. 3A-3H. Gut epithelial barrier dysfunction in Pxr−/− mice requires TLR4 expression and signaling. (A and B) Real-time qPCR analysis of (A) anti-inflammatory, anti-microbial, pro-inflammatory and (B) Tlr gene expressions in Pxr+/+ and Pxr−/− mice jejunum apical enterocytes (n=8-10 mice per group). Data plotted as fold change in Pxr−/− mice relative to mRNA levels in Pxr+/+ mice. (C) Immunoblot shows increased expression of TLR4 in Pxr−/− mice (n=6 mice per group) (left). Immunoblots are representative of three independent experiments. Quantitation of band density was performed with two blots each with three different exposure times (right). (D) Real-time qPCR analysis of key regulatory genes of epithelial barrier function in Pxr$^{+/+}$, Pxr−/−, Tlr4$^{−/−}$ and Pxr−/−/Tlr4−/− mice jejunum apical enterocytes (n=8-10 mice per group). (E) Representative TEM images of Pxr$^{+/+}$, Pxr$^{−/−}$, Tlr4−/− and Pxr−/−/Tlr4−/− mice jejunum showing microvilli (left) and quantitation of average microvillus length (right). (F) Representative TEM images of Pxr+/+, Pxr−/−, Tlr4−/− and Pxr−/−/Tlr4−/− mice jejunum showing cell-cell junctional complex. (G) Enzyme activity assays performed with jejunal apical enterocyte homogenate from Pxr+/+, Pxr−/−, Tlr4−/− and Pxr−/−/Tlr4−/− mice. Data are expressed as fold change relative to Pxr+/+ mice. (H) Serum FITC-dextran permeability assay in Pxr+/+, Pxr−/−, Tlr4−/− and Pxr−/−/Tlr4−/− mice (n=8-10 per group). All graphs show mean values±s.e.m. *P≤0.05; P≤0.01; *P≤0.001, n.s. not significant. Scale bars: E and F, 0.5 µm.
Figures 9A, 9B, 9C:
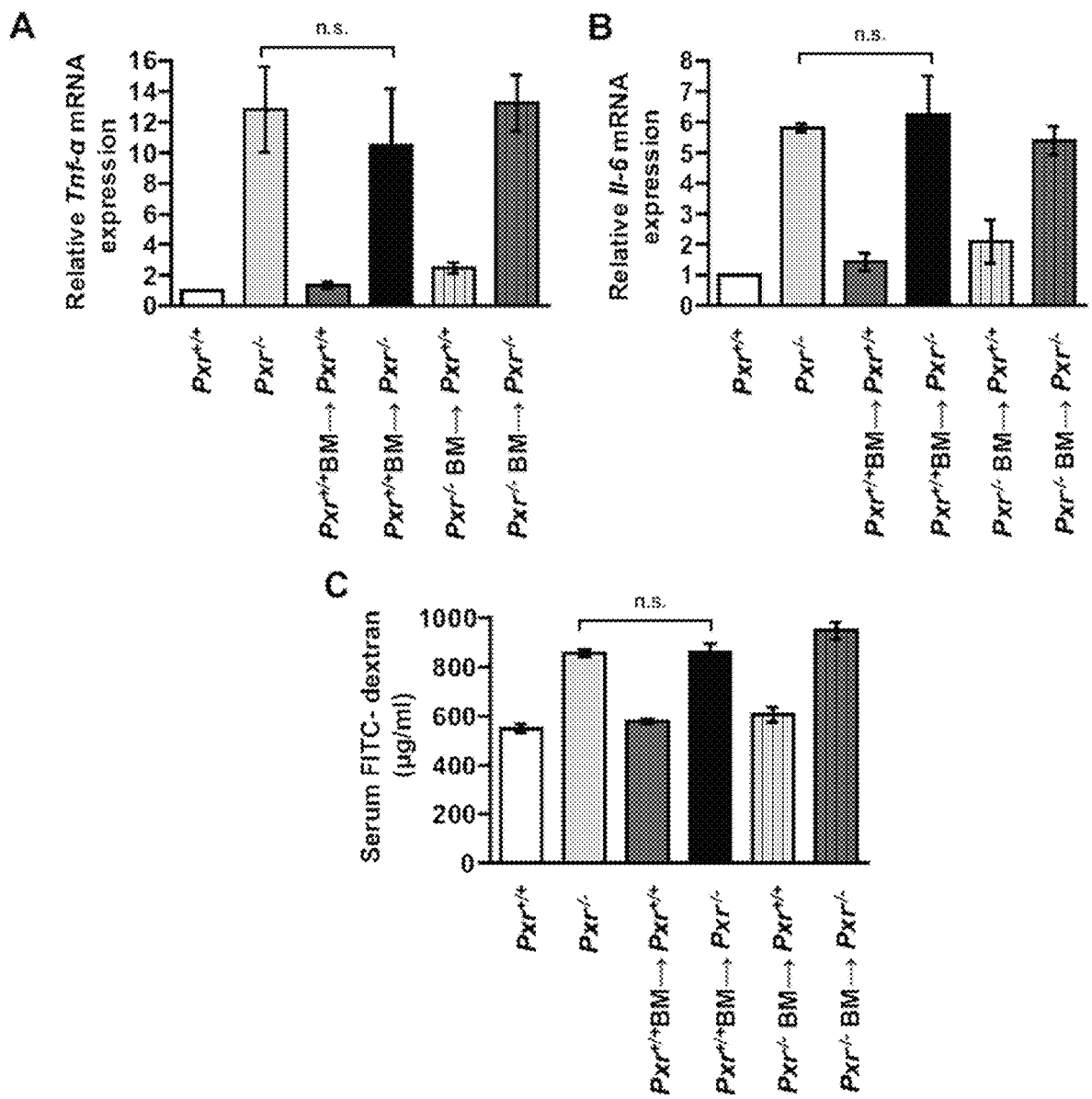
FIG. 9A-9C. Epithelial barrier defects in Pxr−/− mice gut is dependent on non-hematopoietic (epithelium) compartment. (A and B) Real-time qPCR analysis of pro-inflammatory markers (A) Tnf-α and (B) Il-6 was assessed in Pxr+/+ (n=10), Pxr−/− (n=10), Pxr+/+BM Pxr+/+(n=9), Pxr+/+BM Pxr−/− (n=9), Pxr−/− BM Pxr+/+(n=6) and Pxr−/− BM Pxr−/− (n=5) mice jejunal apical enterocytes. Data are expressed as fold change in all mice groups compared to Pxr+/+ mice. (C) In vivo FITC-dextran permeability assay was performed in Pxr+/+(n=10 mice), Pxr−/− (n=10), Pxr+/+BM Pxr+/+(n=9), Pxr+/+BM Pxr−/− (n=9), Pxr−/− BM Pxr+/+(n=6) and Pxr−/− BM Pxr−/− (n=5) mice. All graphs show mean values±s.e.m. n.s. not significant.

Notably, the ultra-structural defects observed in Pxr−/− mice are not due to any gross changes in proliferation or apoptosis of the epithelium. Experiments with bone marrow chimeras between Pxr−/− and Pxr+/+ mice show that immune reconstitution with either Pxr+/+ or Pxr−/− hematopoietic cells have no effect on pro-inflammatory markers and intestinal permeability to FITC-dextran (FIG. 9). Thus, PXR resident in the non-hematopoietic compartment (i.e., epithelium) must be of paramount importance in dictating epithelial barrier dysfunction. To screen for molecular mechanisms that are responsible for barrier dysfunction in Pxr−/− mice, the relative abundance of key host mRNAs encoding proteins involved in inflammation and microbial invasion was determined. Real-time qPCR for anti-inflammatory, antimicrobial and pro-inflammatory markers was performed using total RNA isolated from $Pxr^{+/+}$ and $Pxr^{-/-}$ mice apical enterocytes. In the $Pxr^{-/-}$ mice, there is a significant down-regulation of mRNAs involved in anti-inflammatory and anti-microbial function, along with a concomitant increase in proinflammatory cytokine mRNAs (FIG. 3A).

Figures 10A, 10B, 10C, 10D, 10E, 10F, 10G:
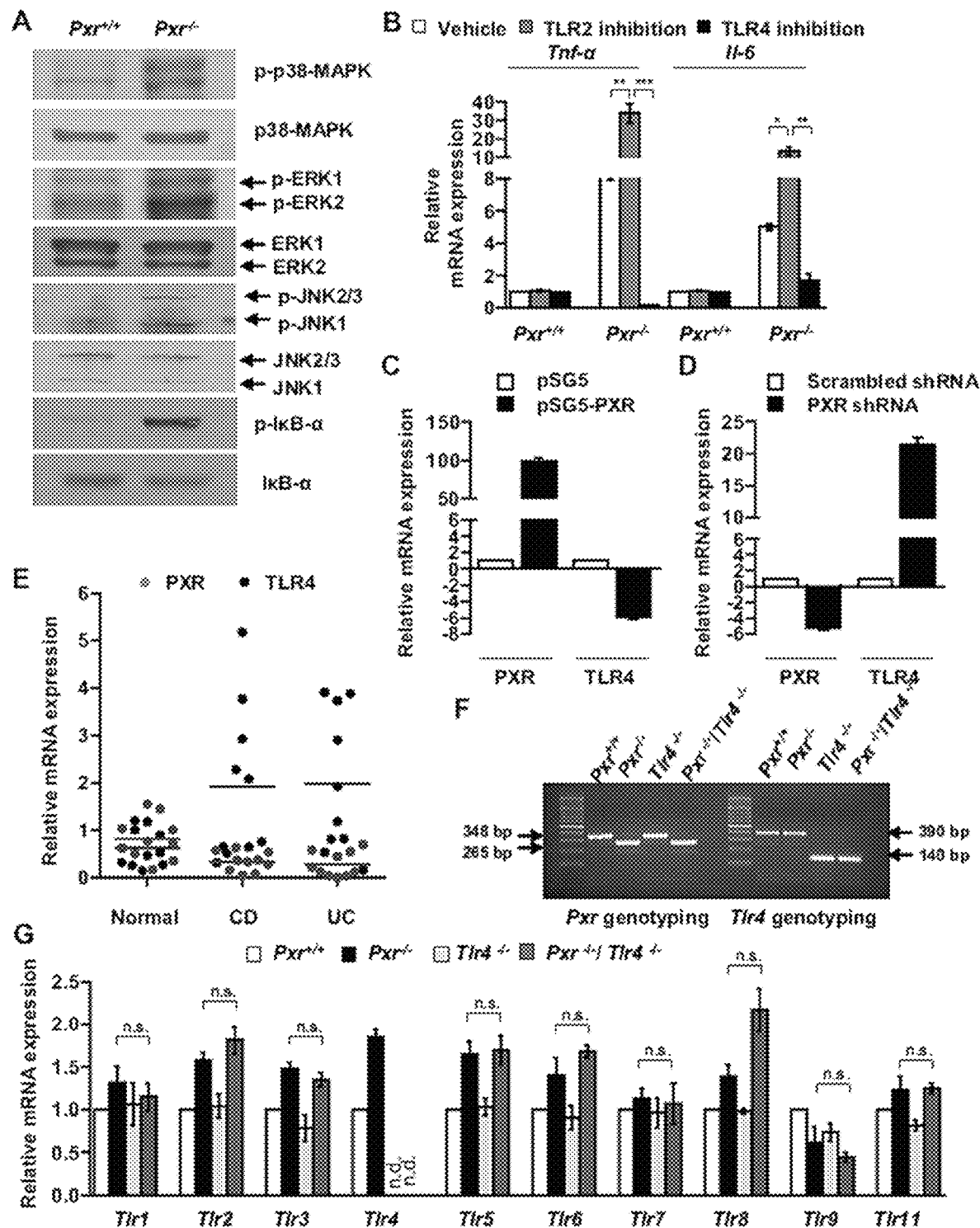
FIG. 10A-10G. TLR4 is responsible for epithelial barrier dysfunction observed in Pxr−/− mice. (A) Immunoblot analysis with pooled jejunal apical enterocyte lysates (n=6 mice per group) prepared from Pxr+/+ and Pxr−/− with indicated antibodies. Blots are representative of three independent experiments. (B) Real-time qPCR analysis of pro-inflammatory markers Tnf-α and Il-6 following ex vivo treatment of Pxr+/+ and Pxr−/− mice jejunum with TLR2 inhibitory antibody (50 μg/ml, eBioscience, 14-9024-82) and TLR4 inhibitor (100 μg/ml, Invivogen, lps-rs). (C) Real-time qPCR analysis of PXR and TLR4 mRNA in undifferentiated Caco-2 cells (UD, have low endogenous PXR expression), transfected with control (pSG5) and PXR overexpression (pSG5-PXR) constructs, respectively. (D) Real-time qPCR analysis of PXR and TLR4 mRNA in LS174T cells (have high endogenous PXR expression), transduced with scrambled and PXR shRNA lentiviral constructs, respectively. (E) Real-time qPCR analysis of PXR and TLR4 mRNA expressions in gut epithelium isolated from normal controls (n=10), Crohn's disease (CD) patients (n=10) and Ulcerative colitis (UC) patients (n=10). **P≤0.01 (ANOVA with Bonferroni test). (F) Genotyping for Pxr and Tlr4 was carried out using polymerase-chain reaction with primers specific to the wild-type and knockout alleles of each gene. In Pxr genotyping, bands at 348 bp and 265 bp indicate the presence of wild-type and knockout alleles, respectively. Similarly, in Tlr4 genotyping, bands at 390 bp and 140 bp indicate the presence of wild-type and knockout alleles, respectively. Parent Pxr−/−/Tlr4+/+ and Pxr+/+/Tlr4−/− mice were crossed with each other to get F1 generation of Pxr+/−/Tlr4+/− mice. Pxr+/−/Tlr4+/− mice (F1) were subsequently crossed that yielded 9.68% of Pxr−/−/Tlr4−/− mice, 58.06% of Pxr+/−/Tlr4+/− mice, 19.36% of Pxr+/−/Tlr4−/− mice and 12.9% of Pxr−/−/Tlr4+/− mice in F2 generation. (G) Real-time qPCR analysis of Tlrs in Pxr+/+, Pxr−/−, Tlr4−/− and Pxr−/−/Tlr4−/− mice jejunum apical enterocytes (n=5 mice per group). The loss of Tlr4 did not result in major reciprocal alterations in other Tlrs in the Pxr−/−/Tlr4−/− double knockout mice. Data are expressed as fold change in all mice groups compared to Pxr+/+ mice (B and G). Fold change in mRNA expressions in figures (C) to (E) was compared to appropriate controls [scrambled shRNA in (C), pSG5 in (D) and normal human control sample #1 in (E)]. All graphs show mean values±s.e.m. *P≤0.05; P≤0.01; *P≤0.001. n.s. not significant; n.d. not detected.

Toll-like receptors (TLRs) were next focused on since they are critical regulators of intestinal barrier function as well as inflammation (23). Real-time qPCR was performed for all ten mammalian (mouse) TLRs. Tlr over-expression was modest (1.2 to 1.8 fold) and variable; however, downstream TLR pathway kinase activation was enhanced in $Pxr^{-/-}$ mice (FIG. 3B and FIG. 10A). Among the TLRs, TLR2 and 4 are expressed on the apical enterocytes and play significant roles in the regulation of gut barrier function (24). To identify the TLRs that may affect inflammatory cytokine mediated barrier function in $Pxr^{-/-}$ mice, $Pxr^{-/-}$ enterocytes were incubated ex vivo with TLR2 and 4 inhibitors. TLR2 inhibition increased Tnf-α and Il-6 mRNA expression in the gut of $Pxr^{-/-}$ mice; conversely, TLR4 inhibition significantly suppressed cytokine mRNA expression (FIG. 10B).

TLR4 was focused on next because it is a critical determinant of LPS signaling in the gut (24-26). The basal expression of TLR4 protein was modestly elevated (~1.8 fold) in $Pxr^{-/-}$ mice. An inverse relationship between PXR and TLR4 mRNA expressions was observed (FIG. 3C and FIG. 10, C to E). To study the role of TLR4 in barrier dysfunction in $Pxr^{-/-}$ mice, the $Pxr^{-/-}$ mice were crossed with $Tlr4^{-/-}$ mice (FIGS. 10, F and G). In comparison with $Pxr^{-/-}$ mice, the abundance of mRNAs encoding key Tj, Aj proteins, pro- and anti-inflammatory cytokines were reversed in $Pxr^{-/-}/Tlr4^{-/-}$ double knockout mice epithelium to levels comparable to those observed in $Pxr^{+/+}$ mice (FIG. 3D).

Figures 11A, 11B, 11C, 11D:
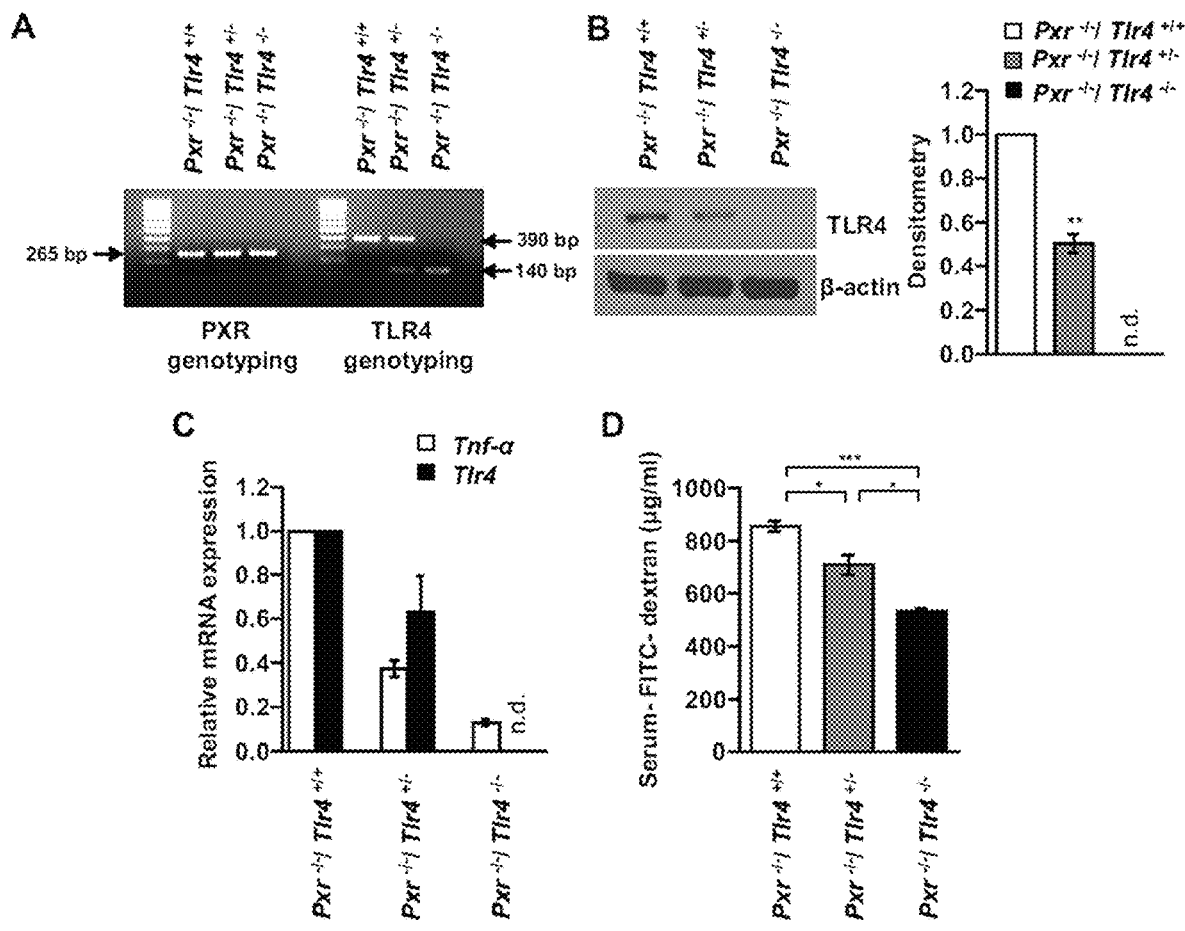
FIG. 11A-11D. Gene dosage effect of TLR4 on epithelial barrier dysfunction observed in Pxr−/− mice. (A) Genotyping for Pxr and Tlr4 was carried out to screen for Pxr−/−/Tlr4+/− heterozygous mice. (B) Immunoblot for TLR4 expression in Pxr−/−/Tlr4+/− heterozygous mice (n=5 mice per group) (left). Quantitation of band density was performed with two blots each with three different exposure times (right). (C) Real-time qPCR analysis of Tnf-α and Tlr4 mRNA expressions in Pxr−/−/Tlr4+/− heterozygous mice (n=5 mice per group). The reduction in Tnf-α mRNA in Tlr4 heterozygotes was found to be 70% [To quantify, differences in Tnf-α mRNA values between Pxr–/–/Tlr4+/+ and Pxr–/–/Tlr4+/–(x) and Pxr–/–/Tlr4+/+ and Pxr–/–/Tlr4–/– (y) were divided (x/y) to obtain the % reduction]. (D) FITC-dextran permeability assay in Pxr–/–/Tlr4+/– heterozygous mice (n=5 mice per group). The reduction in FITC-dextran permeability in Tlr4 heterozygotes was found to be 45%.

Since these markers encode for proteins involved in epithelial junctional complex formation and inflammation, TLR4 may indeed be responsible for the barrier dysfunction observed in $Pxr^{-/-}$ mice. To validate this hypothesis, it was assessed whether the magnitude of Tnf-α mRNA expression and FITC-dextran permeability was Tlr4 gene-dose dependent. Tlr4 heterozygotes (at least ~50% reduction in protein) were generated in $Pxr^{-/-}$ mice background (FIG. 11). Enterocyte Tnf-α mRNA expression and FITC-dextran recovery had similar quantitative reduction (FIG. 11). To further validate the observations regarding genes encoding junctional complex proteins, TEM and immunofluorescence studies were performed. The $Pxr^{-/-}/Tlr4^{-/-}$ double knockout mice have microvilli lengths that are larger than $Pxr^{-/-}$ mice and comparable to that observed for $Pxr^{+/+}$ mice (FIG. 3E). Indeed, the same trends were observed for ultra-structure of junctional complex and immunofluorescence staining for Zo-1 and E-cad (FIG. 3F). The activities of brush border enzymes and FITC-dextran permeability in the $Pxr^{-/-}/Tlr4^{-/-}$ double knockout mice was also similar to that observed in $Pxr^{+/+}$ mice (FIGS. 3, G and H). Additionally, $Pxr^{-/-}/Tlr4^{-/-}$ double knockout mice displayed significantly attenuated damage response to indomethacin. Together, these studies prove that Tlr4 is an essential causative agent in the epithelial barrier defects observed in the $Pxr^{-/-}$ mice.

Figure 4:
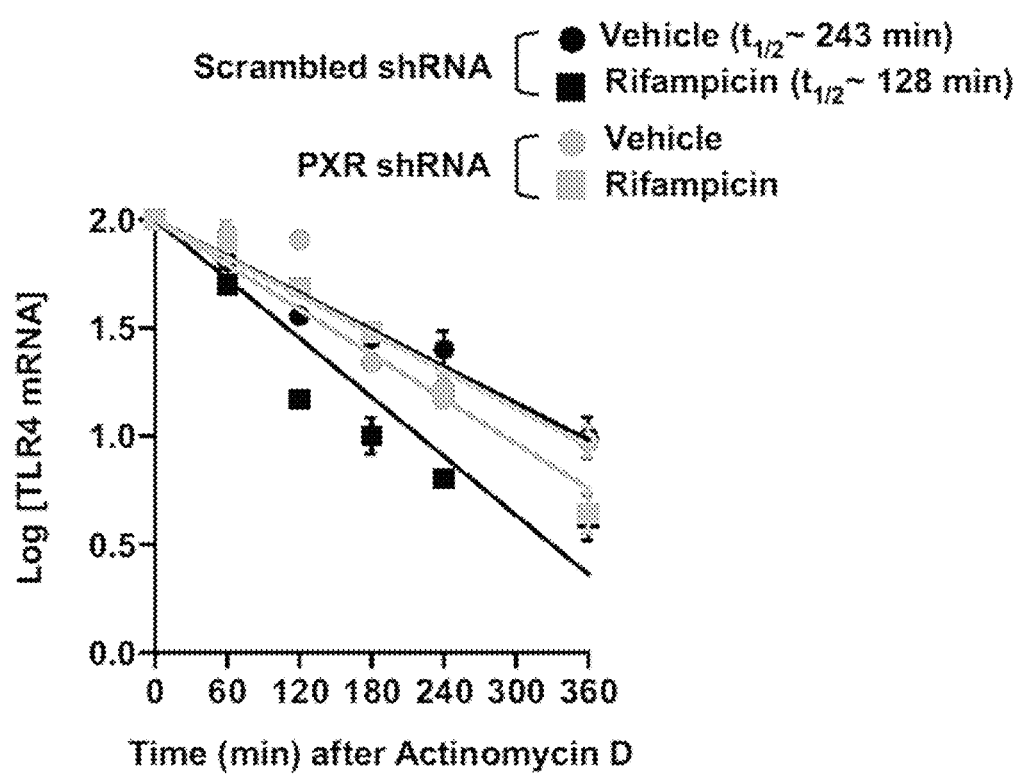
FIG. 4. PXR activation decreases TLR4 mRNA stability. Actinomycin D (20 µg/ml) chase experiment was performed in LS174T cells (transduced with scrambled and PXR shRNA lentiviral constructs) treated with or without rifampicin to evaluate TLR4 mRNA stability. The half-life of TLR4 mRNA was calculated according to the formula: $t_{1/2}=0.693/\kappa$, where $\kappa=\ln(N_0/N_t)t$, where $N_0$ represents TLR4 mRNA expression at t=0 and $N_t$ represents TLR4 mRNA expressions at various time-points. After rifampicin treatment for 48 h, TLR4 mRNA half-life decreased predominantly in shRNA transduced cells compared to PXR shRNA cells.
Figures 12A, 12B, 12C, 12D, 12E:
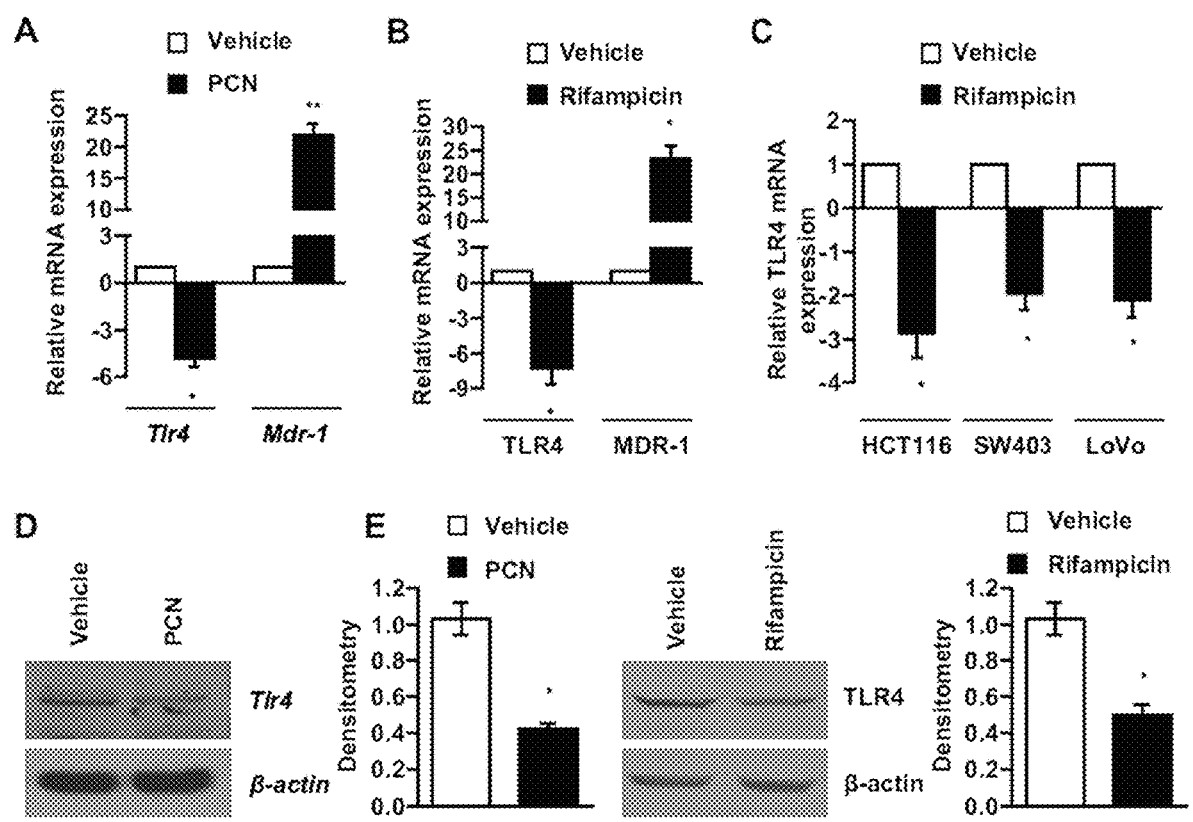
FIG. 12A-12E. Pharmacological activation of PXR decreases TLR4 expression. (A) Real-time qPCR analysis of tlr4 and mdr-1 mRNA expressions in Pxr+/+ mice jejunum apical enterocytes, activated with Pregnenolone 16α-carbonitrile (PCN) (n=8-10 mice per group). Data plotted as fold change in PCN treated group relative to mRNA levels in vehicle (corn oil) treated group. (B) Real-time qPCR analysis of TLR4 and MDR-1 mRNA expressions in differentiated Caco-2 cells (have high endogenous PXR activation), activated with rifampicin. Data plotted as fold change in rifampicin treated group relative to mRNA levels in vehicle (DMSO) treated group. (C) Real-time qPCR analysis of TLR4 mRNA expression in HCT116, SW403 and LoVo cells (intestinal cell lines that expresses PXR), activated with rifampicin. Data plotted as fold change in rifampicin treated group relative to mRNA levels in vehicle (DMSO) treated group. (D) Immunoblot for tlr4 expression in Pxr+/+ mice jejunum apical enterocytes, activated with PCN (n=8-10 mice per group). Quantitation of band density was performed with two blots each with three different exposure times (right). (E) Immunoblot for TLR4 expression in differentiated Caco-2 cells, activated with rifampicin (left). Quantitation of band density was performed with two blots each with three different exposure times (right). All graphs show mean values±s.e.m. *P≤0.05; **P≤0.01.
Figures 13A, 13B, 13C, 13D:
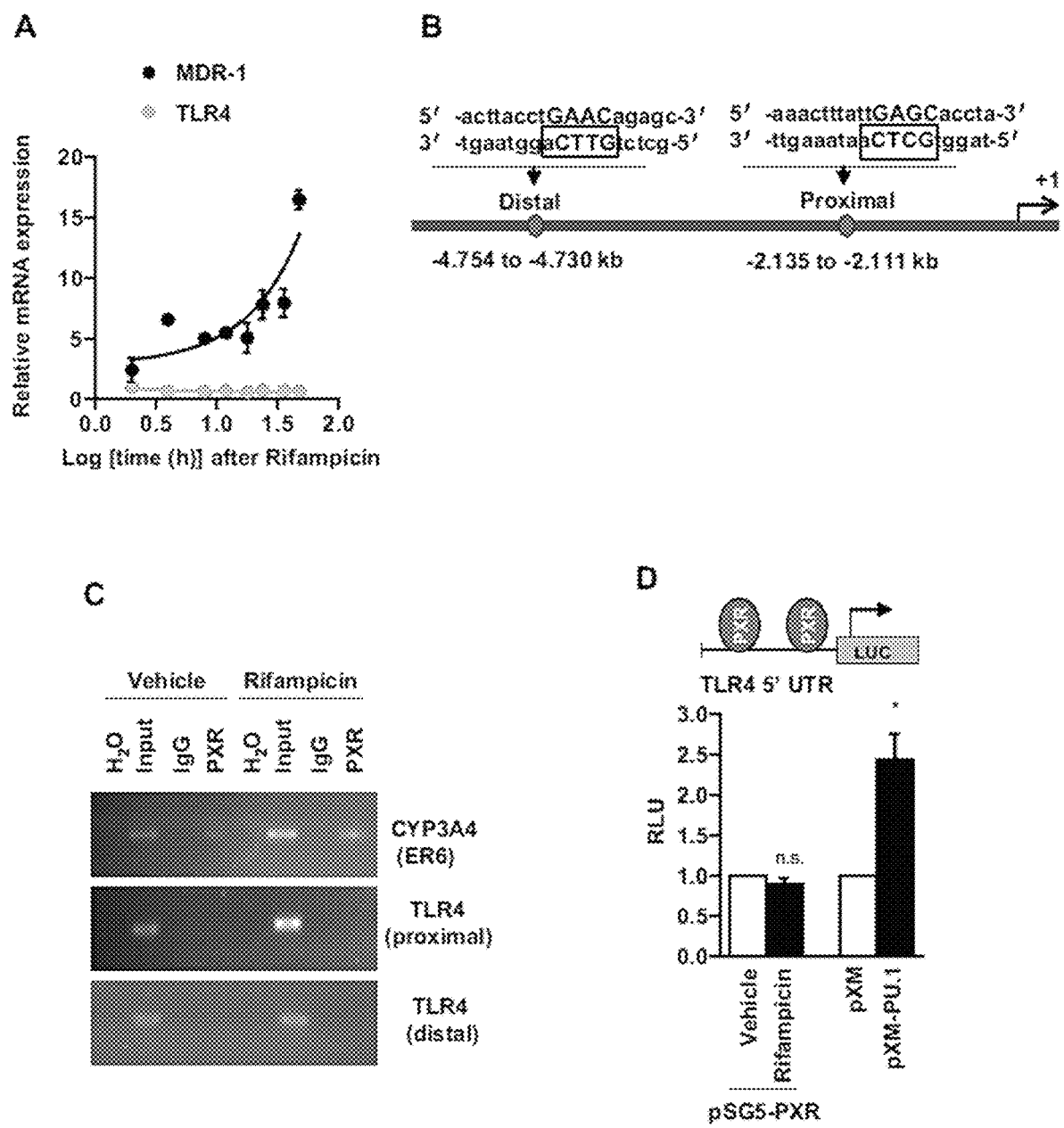
FIG. 13A-13D. PXR mediated regulation of TLR4 expression is not directly dependent on initiation of TLR4 gene transcription. (A) Nuclei of rifampicin treated LS174T cells were isolated at various time-points after rifampicin treatment and used in the nuclear run-on transcription reaction containing 2.5 mM of ATP, CTP, GTP and biotin-14-UTP. After the reaction at 30° C. for 45 minutes, the biotinylated RNA was purified by NeutrAvidin agarose beads and used for cDNA synthesis and real-time qPCR. The transcription efficiency of TLR4 and classical PXR target gene, MDR-1 were analyzed relative to that of β-actin. A steady increase in MDR-1 gene transcription was observed, while TLR4 gene transcription did not change with rifampicin treatment. (B) Bioinformatics analysis revealed two putative PXR DNA binding elements on TLR4 promoter region. The functionality of these putative sites was analyzed by performing Chromatin immunoprecipitation (ChIP) assay. Sequence identifiers: top left, SEQ ID NO:16; bottom left, SEQ ID NO:17; top right, SEQ ID NO:18; bottom right, SEQ ID NO:19. (C) Chromatin immunoprecipitation assay was performed to analyze PXR binding on TLR4 promoter in LS174T cells, treated with or without rifampicin. While PXR binding was observed to classical PXR everted repeat 6 (ER6) DNA binding element on CYP3A4 promoter region with enhanced binding in rifampicin treated cells, PXR did not bind to the putative binding sites on TLR4 promoter. IgG antibody served as a negative control. (D) Luciferase transcription assay was performed in 293T cells, transfected with TLR4 promoter luciferase construct, PXR expression plasmids and expression plasmid for a known positive transcriptional regulator of TLR4, PU.1. Rifampicin was used as a PXR agonist. Data expressed as fold change in RLU compared to untreated and empty vector (pXM) transfected cells, respectively. RLU, relative light unit. All graphs show mean values±s.e.m. *P≤0.05. n.s. not significant.

An inverse relationship between PXR and TLR4 was previously observed and furthermore, a decrease in TLR4 expression secondary to PXR activation was also observed (FIG. 12, A to E). Thus, the molecular mechanisms governing PXR mediated TLR4 regulation were investigated. PXR activation did not have a direct effect on the initiation of TLR4 gene transcription (FIG. 13, A to D). PXR activation in vitro decreased TLR4 mRNA stability (FIG. 4A). In addition, PXR bound to the 3' untranslated region of TLR4 mRNA (FIG. 4B). While, it is still possible that PXR indirectly could regulate TLR4 gene transcription through other mechanisms (e.g., trans-repression), these studies have uncovered a novel mechanism of PXR action on TLR4 mRNA stability.

The present data implicate epithelial PXR as a central regulator of TLR4 mediated control of the gut barrier function. This regulation is intrinsically associated with gut commensals, specifically those involved with the metabolism of tryptophan with production of indoles and specific metabolites. It was hypothesized that this association is tightly regulated to ensure "fine-tuning" of TLR4 expression in the gut at levels appropriate to the abundance of LPS and perhaps other microbial-derived ligands. For homeostasis, all three components of this system (indole secreting gut commensals, epithelial PXR expression, and TLR4) must be at appropriate levels for a given host a lack of IPA or PXR or an excess of TLR4 can lead to gut barrier dysfunction. In fact, compromised gut barrier function has been implicated in the pathogenesis of several disease states (e.g., type I diabetes, asthma, autism, acne, allergies etc.) including IBD (5). Hence, search for effective treatment options to prevent gut epithelial barrier defects may have broader implications beyond IBD. Moreover, the data in epithelial cells complement parallel nuclear receptor driven pathways in gut immune cells that regulate barrier function (27, 28). Thus, taken together, these observations provide important chemical biology steps toward a more comprehensive understanding of gut barrier function.

TABLE 1

Summary of scores for IPA and indole docked either individually or concurrently to hPXR and mPXR structures.

| | IPA | | Indole | |
|---|---|---|---|---|
| Organism | −Indole | +Indole | −IPA | +IPA |
| hPXR | 40.81 | 54.63 | 36.08 | 56.00 |
| mPXR | 43.82 | 61.21 | 42.93 | 62.23 |

Example 2

Tryptophanase is a multifunctional enzyme found exclusively in bacteria. This enzyme is responsible for beta-elimination of a catabolite, tryptophan, to form indoles, which then serve as substrates for further modifications in certain bacteria (e.g., IPA in *C. sporogenes*, IAA in *E. coli*, and other species) (Proc Natl Acad Sci USA. 2009 Mar. 10; 106(10):3698-703; Microbiology 2006 August; 152(Pt 8):2421-3; hereby incorporated by reference in its entirety). The Tna operon contains two genes: promoter proximal gene, tnaA, encodes tryptophanase, while tnaB, is required for low-affinity tryptophan permease activity. The Tna *E. coli* operon is induced by tryptophan and is subject to catabolite repression (e.g., cAMP and other catabolites). Thus, developing constitutively-expressing strains will eliminate variability of expression due to human diet (from catabolites). One strategy is to start with *E. coli* and reproducing the isolation of TnaC (this removes tryptophan-induced antitermination) (J Bacteriol 164, 731-740, 1985; hereby incorporated by reference in its entirety). For example, *E. coli* K-12 can be used with ethyl methanesulfonate and 2-aminopurine mutagenesis as described by Miller (Experiments in Molecular Genetics. Cold Spring Harbor Laboratory, NY 19725; hereby incorporated by reference in its entirety). However, gene knockout strategies by homologous recombination are now a simpler route (e.g. see www.sigmaaldrich.com/life-science/molecular-biology/molecular-biology-products.html?TablePage=17058681) within the TnaC as well as the distal rut gene (J Bacteriol 172, 3100-3107, 1990) both of which will give constitutive expression of the operon. Mutations of the boxA and the rut site are also encompassed and readily achievable. (See also Rho-Dependent Transcription Termination in the tna Operon of *Escherichia coli*: Roles of the boxA Sequence and the rut Site, 182 J. Bacteriol. 3981-88 (2000); hereby incorporated by reference in its entirety).

Example 3

*C. sporogenes*, which Makes Indoles and IPA, Protects Against Indomethacin Induced Intestinal Injury by Activating PXR.

Figures 14A, 14B, 14C, 14D, 14E, 14F, 14G, 14H, 14I:
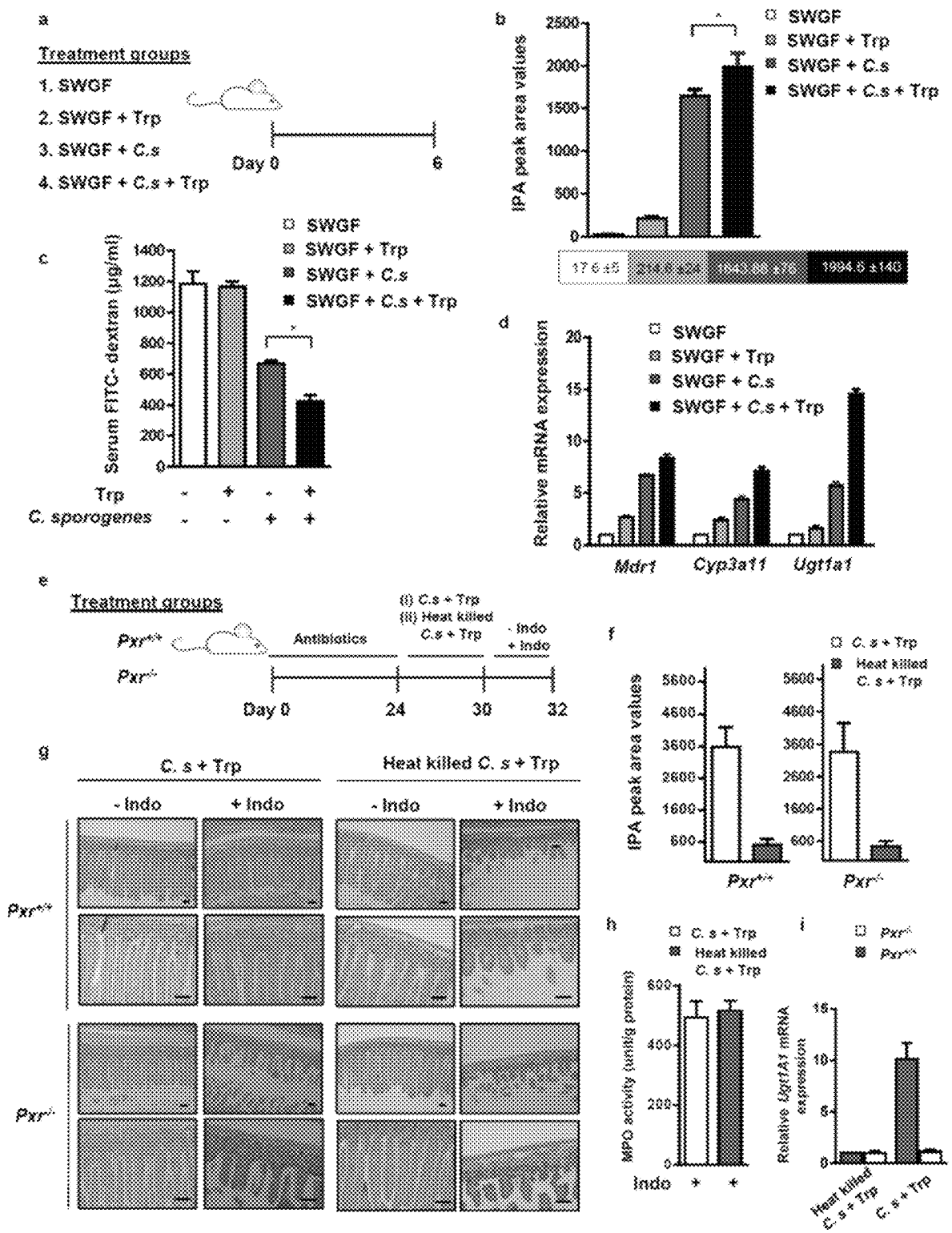
FIG. 14A-14I. Commensal C. sporogenes reconstitution decreases intestinal permeability and inflammation in a PXR-dependent manner in mice. (A) Schematic of germ free mouse treatment schedule. Four (4) treatment groups are shown. 1. Swiss Webster Germ Free mice (SWGF) group, administered 100 μl LB and 100 μl sterilized water by oral gavage. 2. SWGF+tryptophan (Trp) group, administered 100 μl LB+L-tryptophan. 3. SWGF+C. sporogenes (C.s) group, administered C.s by oral gavage and 4. SWGF+C.s+Trp group, administered C.s and Trp by oral gavage. All the treatments were scheduled for six sequential days. (B) Plasma IPA peak area intensity values plotted by treatment group as illustrated in the schema (A). Boxes show mean±s.e.m. values pertaining to each treatment group. (C) Serum FITC-dextran recovery in treatment groups illustrated in schema (A). (D) Real-time qPCR analysis of Mdr1, Cyp3a11 and Ugt1a1 mRNA expression in small intestinal mucosa from schema (A). (E) Schematic of commensal depletion and C. sporogenes reconstitution experiment in Pxr+/+ and Pxr–/– mice. (F) Plasma IPA peak area intensity values plotted by treatment groups as illustrated in the schema (E). (G) Hematoxylin and eosin staining of C. sporogenes+L-tryptophan and Heat killed C. sporogenes+L-tryptophan exposed Pxr+/+ and Pxr–/– mice jejunum cross-sections in accordance with schema (E). Scale bars, 50 μm. (H) Jejunal MPO activity (unit/g of total protein) in treatment groups from schema (E) as illustrated. (I) Realtime qPCR analysis of Ugt1a1 mRNA expression in small intestinal mucosa from schema (E). All graphs show mean values±s.e.m. *P≤0.02 (Student's t-test), (n=6 per group).
Figure 15:
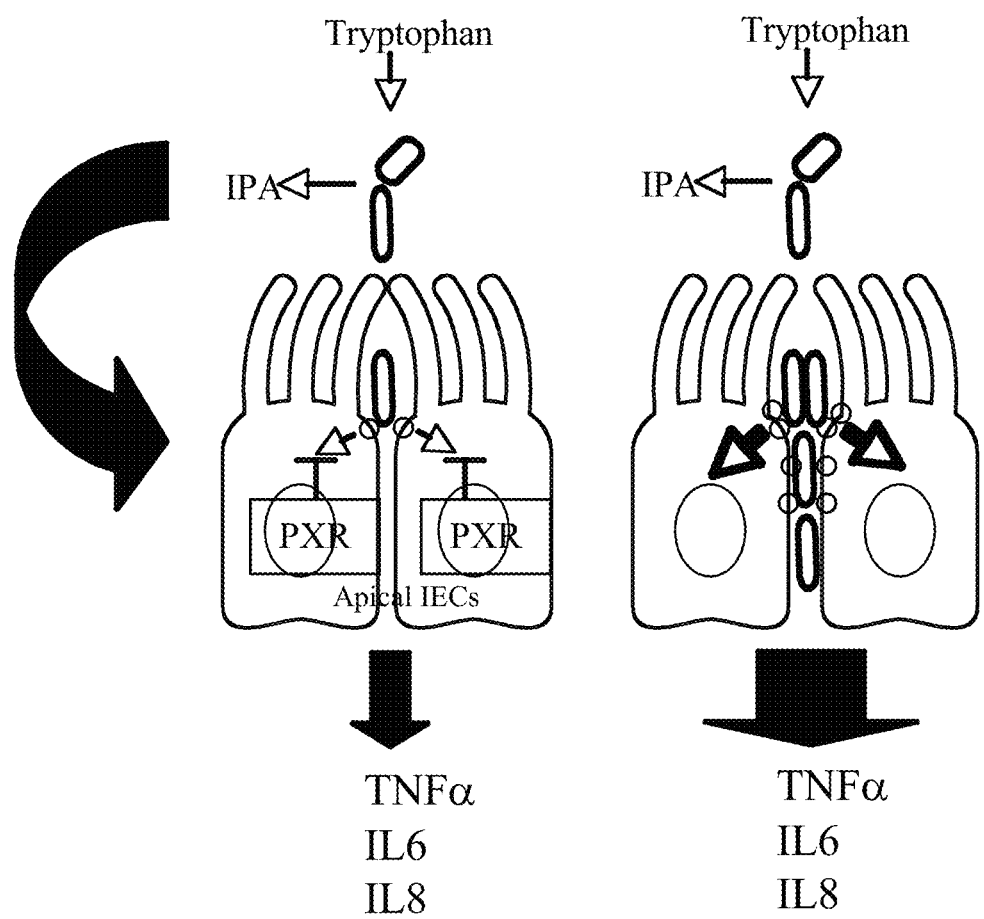
FIG. 15. Model for regulation of gut barrier function by IPS. In the small intestines, where PXR is expressed in intestinal epithelial cells in a crypt-villus gradient, in homeostasis, dietary tryptophan-derived bacterial metabolites (i.e. indoles and indole metabolites in particular indole 3 propionic acid or IPA) tonically activate PXR and induce a down-regulation of the Toll-like Receptors (thin black arrows within the cell), in particular TLR4, and its downstream signaling pathway. This results in modulating the abundance of TNF-α, which in turn modulates intestinal barrier function (i.e. permeability). In the context of an inappropriate increase in inflammatory signals (e.g., infection), suppression of PXR, and/or excess loss of dietary modulators (e.g., tryptophan), and/or specific indole metabolizing bacteria (e.g., antibiotics) results in increased permeability (left inset white arrow), thus exacerbating underlying disease predisposition and pathology (thick black arrow inside and outside cell). In this model, restitution of signaling homeostasis, either by reconstituting intestinal loss of indole-metabolite producing bacteria and/or PXR activating bacterial metabolites (i.e. IPA), could result in abrogating pro-inflammatory signals and loss of barrier permeability in the context of intestinal inflammation.

For validation of ex vivo experiments demonstrating IPA effects on junctional regulators, *C. sporogenes* was co-administered to germ-free mice in the presence or absence of L-tryptophan (FIG. 14*a*). *C. sporogenes* inoculation led to production of IPA in vivo (thus, it was assumed that indoles were present) (FIG. 14*b*). Germ-free mice exposed to *C. sporogenes* had a significant reduction in FITC-dextran recovery from the serum and this was further reduced in the presence of L-tryptophan dosing (FIG. 14*c*). The mice intestinal mucosa exposed to *C. sporogenes* demonstrated significant induction of PXR target genes (Mdr1, Cyp3a11, Ugt1a1), which was further augmented in the presence of L-tryptophan (FIG. 14*d*). To validate that IPA was indeed driving the anti-inflammatory response in vivo directly via PXR, intestinal commensal-depleted Pxr+/+ and Pxr−/− mice were exposed to live or heat-killed *C. sporogenes*. All mice were subsequently exposed to indomethacin (FIG. 14*e*). Only live *C. sporogenes*, but not the heat-killed bacterial inoculation, led to production of IPA in vivo (FIG. 14*f*). There was a significant reduction in the histologic injury and in mucosal myeloperoxidase (MPO) enzyme activity (FIG. 14*g,h*). Furthermore, in these mice, intestinal mucosa exposed to the *C. sporogenes* had significant induction of PXR target gene (Ugt1a1) when compared to mice exposed to the heat-killed strain (FIG. 14*i*). No such effects were observed in Pxr−/− mice (FIG. 14*f-i*).

IPA is not a AhR Receptor (Related to PXR) Agonist.

The combination of indole and IPA also activated other orphan nuclear receptors that play a role in intestinal barrier protection (e.g., farnesoid x receptor), suggesting a crucial role of indoles in maintaining intestinal barrier function involving multiple nuclear receptors (10). However, hPXR activation was greater in comparison to other nuclear receptors tested. More importantly, as specific indoles have been shown to activate the aryl hydrocarbon receptor (AhR) (63), no activation was observed of AhR by IPA.

REFERENCES

1. A. Kaser, S. Zeissig, R. S. Blumberg, *Annu Rev Immunol* 28, 573 (2010).
2. J. R. Turner, *Nat Rev Immunol* 9, 799 (2009).
3. A. Krack, R. Sharma, H. R. Figulla, S. D. Anker, *Eur Heart J* 26, 2368 (2005).
4. O. Vaarala, *Curr Opin Gastroenterol* 24, 701 (2008).
5. Z. Liu, N. Li, J. Neu, *Acta Paediatr* 94, 386 (2005).
6. W. R. Wikoff et al., *Proc Natl Acad Sci USA* 106, 3698 (2009).
7. J. P. Danaceau, G. M. Anderson, W. M. McMahon, D. J. Crouch, *J Anal Toxicol* 27, 440 (2003).
8. T. Bansal, R. C. Alaniz, T. K. Wood, A. Jayaraman, *Proc Natl Acad Sci USA* 107, 228 (2010).
9. Z. Zhu et al., *J Biomol Screen* 9, 533 (2004).
10. T. Inagaki et al., *Proc Natl Acad Sci USA* 103, 3920 (2006).
11. F. Wang et al., *Gastroenterology* 131, 1153 (2006).
12. P. D. Martino, R. Fursy, L. Bret, B. Sundararaju, R. S. Phillips, *Can J Microbiol* 49, 443 (2003).
13. R. S. Phillips, E. W. Miles, L. A. Cohen, *Biochemistry* 23, 6228 (1984).
14. M. Venkatesh et al., *Mol Pharmacol* 80, 124 (2011).
15. Y. M. Shah, X. Ma, K. Morimura, I. Kim, F. J. Gonzalez, *Am J Physiol Gastrointest Liver Physiol* 292, G1114 (2007).
16. C. Zhou et al., *J Clin Invest* 116, 2280 (2006).
17. R. R. Ettarh, K. E. Carr, *J Anat* 189 (Pt 1), 51 (1996).
18. D. R. Clayburgh et al., *J Clin Invest* 115, 2702 (2005).
19. H. Zhao, M. C. Montalto, K. J. Pfeiffer, L. Hao, G. L. Stahl, *J Appl Physiol* 93, 338 (2002).
20. T. Roger et al., *Proc Natl Acad Sci USA* 106, 2348 (2009).
21. Y. Ohtsuka, I. R. Sanderson, *Pediatr Res* 53, 143 (2003).
22. C. M. Van Itallie, J. M. Anderson, *Annu Rev Physiol* 68, 403 (2006).
23. M. Asquith, F. Powrie, *J Exp Med* 207, 1573 (2010).
24. E. Cario, *Inflamm Bowel Dis* 16, 1583 (2010).
25. M. M. Fort et al., *J Immunol* 174, 6416 (2005).
26. M. T. Abreu et al., *J Immunol* 167, 1609 (2001).
27. E. A. Kiss et al., *Science* 334, 1561 (2011).
28. J. S. Lee et al., *Nat Immunol* 13, 144 (2011).
29. J. L. Staudinger et al., *Proc Natl Acad Sci USA* 98, 3369 (2001).
30. W. Xie et al., *Nature* 406, 435 (2000).
31. T. Asano et al., *J Pharmacol Exp Ther* 330, 458 (2009).
32. M. M. Weiser, *J Biol Chem* 248, 2542 (1973).
33. H. Huang et al., *Oncogene* 26, 258 (Jan. 11, 2007).
34. R. F. Goldberg et al., *Proc Natl Acad Sci USA* 105, 3551 (2008).
35. A. Dahlqvist, *Anal Biochem* 7, 18 (1964).
36. T. Nagatsu, M. Hino, H. Fuyamada, T. Hayakawa, S. Sakakibara, *Anal Biochem* 74, 466 (1976).
37. L. A. Pfister et al., *Ann Neurol* 47, 329 (2000).
38. A. Kaser et al., *Cell* 134, 743 (2008).
39. M. Zhao et al., *Proc Natl Acad Sci USA* 98, 9814 (2001).
40. D. Song et al., *Curr Microbiol* 52, 69 (2006).
41. R. E. Watkins et al., *Biochemistry* 42, 1430 (2003).
42. A. Sali, T. L. Blundell, *J Mol Biol* 234, 779 (1993).
43. G. Jones, P. Willett, R. C. Glen, A. R. Leach, R. Taylor, *J Mol Blot* 267, 727 (1997).
44. S. Kortagere et al., *Environ Health Perspect* 118, 1412 (2010).
45. S. Ekins et al., *PLoS Comput Biol* 5, e1000594 (2009).
46. S. Kortagere, D. Chekmarev, W. J. Welsh, S. Ekins, *Pharm Res* 26, 1001 (2009).
47. T. S. Olson et al., *J Exp Med* 203, 541 (2006).
48. D. Sun, M. Melegari, S. Sridhar, C. E. Rogler, L. Zhu, *Biotechniques* 41, 59 (2006).
49. H. Wang et al., *J Clin Invest* 121, 3220 (2011).
50. M. X. Zhang et al., *Proc Natl Acad Sci USA* 102, 16967 (2005).
51. J. D. Nelson, O. Denisenko, K. Bomsztyk, *Nat Protoc* 1, 179 (2006).
52. Chawla, A., Repa, J. J., Evans, R. M., and Mangelsdorf, D. J. (2001) Nuclear receptors and lipid physiology: opening the X-files. Science 294, 1866-70.
53. Gronemeyer, H., Gustafsson, J. A., and Laudet, V. (2004) Principles for modulation of the nuclear receptor superfamily. Nat Rev Drug Discov 3, 950-64.
54. Mangelsdorf, D. J., and Evans, R. M. (1995) The RXR heterodimers and orphan receptors. Cell 83, 841-50.
55. Mangelsdorf, D. J., Thummel, C., Beato, M., Herrlich, P., Schutz, G., Umesono, K., Blumberg, B., Kastner, P., Mark, M., Chambon, P., and et al. (1995) The nuclear receptor superfamily: the second decade. Cell 83, 835-9.
56. Ingraham, H. A., and Redinbo, M. R. (2005) Orphan nuclear receptors adopted by crystallography. Curr Opin Struct Biol 15, 708-15.

57. McDonnell, D. P., Connor, C. E., Wijayaratne, A., Chang, C. Y., and Norris, J. D. (2002) Definition of the molecular and cellular mechanisms underlying the tissue-selective agonist/antagonist activities of selective estrogen receptor modulators. Recent Prog Horm Res 57, 295-316.
58. Shiau, A. K., Barstad, D., Loria, P. M., Cheng, L., Kushner, P. J., Agard, D. A., and Greene, G. L. (1998) The structural basis of estrogen receptor/coactivator recognition and the antagonism of this interaction by tamoxifen. Cell 95, 927-937.
59. Kliewer, S. A., Moore, J. T., Wade, L., Staudinger, J. L., Watson, M. A., Jones, S. A., McKee, D. D., Oliver, B. B., Willson, T. M., Zetterstrom, R. H., Perlmann, T., and Lehmann, J. M. (1998) An orphan nuclear receptor activated by pregnanes defines a novel steroid signaling pathway. Cell 92, 73-82.
60. Fayard, E., Auwerx, J., and Schoonjans, K. (2004) LRH-1: an orphan nuclear receptor involved in development, metabolism and steroidogenesis. Trends Cell Biol 14, 250-60.
61. Bertilsson, G., Heidrich, J., Svensson, K., Asman, M., Jendeberg, L., Sydow-Backman, M., Ohlsson, R., Postlind, H., Blomquist, P., and Berkenstam, A. (1998) Identification of a human nuclear receptor defines a new signaling pathway for CYP3A induction. Proceedings of the National Academy of Sciences of the United States of America 95, 12208-13.
62. Mani S, Huang H, Sundarababu S, et al. Activation of the steroid and xenobiotic receptor (human pregnane X receptor) by nontaxane microtubule-stabilizing agents. Clin Cancer Res. 2005 Sep. 1; 11(17):6359-69.
63. Denison M S, Nagy S R. Activation of the aryl hydrocarbon receptor by structurally diverse exogenous and endogenous chemicals. Annual review of pharmacology and toxicology, 43: 309-334. (2003).

Example B

Symbiotic Bacterial Metabolites Regulate Gastrointestinal Barrier Function Via the Xenobiotic Sensor PXR and Toll-Like Receptor 4

Example B was published by inventors Sridhar Mani and Subhajit Mukherjee and colleagues as Venkatesh, M. et al., Symbiotic Bacterial Metabolites Regulate Gastrointestinal Barrier Function via the Xenobiotic Sensor PXR and Toll-like Receptor 4, Immunity 41: 296-310, Aug. 21, 2014, Epub 2014 Jul. 24, a copy of which is submitted in connection with this application.

The results illustrate that microbial specific indoles regulate intestinal barrier function through the xenobiotic sensor, pregnane X receptor (PXR). Indole 3-propionic acid (IPA), in the context of indole, serves as a ligand for PXR in vivo and down-regulates enterocyte TNF-α while up-regulating junctional protein-coding mRNAs. PXR null (Pxr$^{-/-}$) mice exhibit a distinctly "leaky" gut physiology coupled with up-regulation of the Toll-like receptor (TLR) signaling pathway. These defects in the epithelial barrier are corrected in Pxr$^{-/-}$/Tlr4$^{-/-}$ double-knockout mice. The results demonstrate that a direct chemical communication between the intestinal symbionts and PXR regulates mucosal integrity through a pathway that involves luminal sensing and signaling by TLR4.

Example C

Model for Regulation of Gut Barrier Function by IPA

Indole is exclusively produced by intestinal bacteria. Upon the availability of L-tryptophan, the repressed tryptophanase operon (trp ABCDE) and tna operon (tnaCAB), are induced. In the absence of L-tryptophan, the expression of the trp operon is elevated, whereas the expression of the tna operon consisting of TnaC (24 aa leader peptide, TnaL), TnaA (tryptophanase; EC4.1.99.1), and TnaB (permease) is repressed due to transcription-termination factor (Rho)-dependent termination at the tna operon. Thus, when tryptophan content is low, TnaA and TnaB are low, and indole concentrations are low. However, when tryptophan concentrations increase in the media, (Rho)-dependent transcriptional termination is no longer present, there is accumulation of TnaC-peptidyl-tRNA$^{Pro}$ (the C-terminal peptide is proline) accumulation, increase in TnaA and TnaB, so indole concentrations rise (E. coli pathway) (1-3). In addition, permeases (Mtr, TnaB, and AroP) have specific roles in tryptophan transport: it is clear that Mtr is the major importer of indoles, while TnaB (critical permease), Mtr and AroP participate in tryptophan import. The later permeases, AcrE and AcrF are also involved in export of indoles. Thus, indoles generated in one species can cross cell membrane boundaries of permissive cells and participate in interkingdom signaling. A recent review paper discuss the type of bacteria and species that encode the tnaA gene and its ramifications (1). There is also a significant influence of the environment, other than the availability of L-tryptophan on TnaA expression (e.g., cell density, high pH, low glucose availability) (3). The indoles have been implicated in interkingdom signaling among bacteria. Its role is central in regulating (inhibiting) biofilm formation, motility, chemotaxis, and cell adherence (notably all these functions are altered in pathophysiologic states such as inflammatory bowel disease, perhaps signifying loss of indole-mediated homeostasis). Other effects of indoles include regulation (enhancement) of plasmid stability, virulence and drug resistance. Indoles might be putative quorum-sensing molecules although this has yet to be proven.

Additional direct evidence that tryptophan metabolism is altered in inflammatory bowel disease (IBD) come from the observation that L-tryptophan supplementation of mice exposed to inflammatory toxins (DSS, TNBS) ameliorates inflammatory indices in the intestines (4,5). Colitic mice have reduced indole metabolites (6). In humans, urinary excretion of tryptophan is increased, resulting in low serum tryptophan levels; this is further buttressed by enhanced Indoleamine 2,3-dioxygenase (IDO) expression in inflamed enterocytes and rapid tryptophan catabolism in the intestines, resulting in low serum tryptophan but also markedly increased serum kyneurine:tryptophan ratio (5, 7-15) and end metabolites (16). However, fecal tryptophan content is elevated suggesting a block in microbial tryptophan metabolism (17). Similar results have been found in mice with radiation-mediated intestinal damage, in that, serum indole and indole metabolites (IPA) are inversely correlated with the extent of intestinal inflammation (18-19). The observation that IPA is inversely related to systemic inflammation in overweight individuals (20) as well as the reversal of IPA levels (increased) upon administration of anti-inflammatory dietary interventions to humans (21) adds further proof of the importance of IPA in inflammation. Additionally, environmental factors, beyond availability of tryptophan influence the coding of TnaA. For example, it has been demonstrated that the intestinal intraluminal pH in patients with IBD and rodent model systems is low (22-24). Since high pH induces TnaA, low intraluminal pH in IBD likely represses TnaA expression, thus shutting off indole production regardless of the availability of tryptophan. While bacterial cell density induces TnaA, and that the mean density of mucosal biofilms is 2-fold higher in patients with IBD than normal controls, specific microbiota producing indoles may be attenuated by the inflammatory process, reducing diversity and microbial (indole)-specific biofilm density (25). Finally, diets high in refined sugar have been associated with IBD susceptibility (26); high glucose represses TnaA expression, suggesting loss of indoles in IBD (3).

Thus, based on available evidence, ipa to tryptophan ratios can serve as a biomarker for intestinal inflammatory states, where, e.g., ipa/trp<1 indicates inflammation and ipa/trp>1 indicates homeostasis.

References for Example C

1. Lee J H, Lee J. Indole as an intercellular signal in microbial communities. FEMS microbiology reviews. 2010; 34(4):426-44.
2. Gong F, Ito K, Nakamura Y, Yanofsky C. The mechanism of tryptophan induction of tryptophanase operon expression: tryptophan inhibits release factor-mediated cleavage of TnaC-peptidyl-tRNA(Pro). Proceedings of the National Academy of Sciences of the United States of America. 2001; 98(16):8997-9001.
3. Han T H, Lee J H, Cho M H, Wood T K, Lee J. Environmental factors affecting indole production in *Escherichia coli*. Research in microbiology. 2011; 162(2):108-16.
4. Kim C J, Kovacs-Nolan J A, Yang C, Archbold T, Fan M Z, Mine Y. 1-Tryptophan exhibits therapeutic function in a porcine model of dextran sodium sulfate (DSS)-induced colitis. The Journal of nutritional biochemistry. 2010; 21(6):468-75.
5. Shizuma T, Mori H, Fukuyama N. Protective effect of tryptophan against dextran sulfate sodium-induced experimental colitis. The Turkish journal of gastroenterology: the official journal of Turkish Society of Gastroenterology. 2013; 24(1):30-5.
6. Shiomi Y, Nishiumi S, Ooi M, Hatano N, Shinohara M, Yoshie T, et al. GCMS-based metabolomic study in mice with colitis induced by dextran sulfate sodium. Inflamm Bowel Dis. 2011; 17(11):2261-74.
7. Barcelo-Batllori S, Andre M, Servis C, Levy N, Takikawa O, Michetti P, et al. Proteomic analysis of cytokine induced proteins in human intestinal epithelial cells: implications for inflammatory bowel diseases. Proteomics. 2002; 2(5):551-60.
8. Beeken W L. Serum tryptophan in Crohn's disease. Scand J Gastroenterol. 1976; 11(7): 735-40.
9. Cherayil B J. Indoleamine 2,3-dioxygenase in intestinal immunity and inflammation. Inflamm Bowel Dis. 2009; 15(9):1391-6.
10. Ferdinande L, Demetter P, Perez-Novo C, Waeytens A, Taildeman J, Rottiers I, et al. Inflamed intestinal mucosa features a specific epithelial expression pattern of indoleamine 2,3-dioxygenase. International journal of immunopathology and pharmacology. 2008; 21(2):289-95.
11. Lin H M, Barnett M P, Roy N C, Joyce N I, Zhu S, Armstrong K, et al. Metabolomic analysis identifies inflammatory and noninflammatory metabolic effects of genetic modification in a mouse model of Crohn's disease. Journal of proteome research. 2010; 9(4):1965-75.
12. Lin H M, Edmunds S I, Helsby N A, Ferguson L R, Rowan D D. Nontargeted urinary metabolite profiling of a mouse model of Crohn's disease. Journal of proteome research. 2009; 8(4):2045-57.
13. Minderhoud I M, Oldenburg B, Schipper M E, ter Linde J J, Samsom M. Serotonin synthesis and uptake in symptomatic patients with Crohn's disease in remission. Clinical gastroenterology and hepatology: the official clinical practice journal of the American Gastroenterological Association. 2007; 5(6):714-20.
14. Tones M I, Lopez-Casado M A, Lorite P, Rios A. Tryptophan metabolism and indoleamine 2,3-dioxygenase expression in coeliac disease. Clinical and experimental immunology. 2007; 148(3):419-24.
15. Wolf A M, Wolf D, Rumpold H, Moschen A R, Kaser A, Obrist P, et al. Overexpression of indoleamine 2,3-dioxygenase in human inflammatory bowel disease. Clinical immunology (Orlando, Fla.). 2004; 113(1):47-55.
16. Yau Y Y, Leong R W, Shin S, Bustamante S, Pickford R, Hejazi L, et al. Bimodal plasma metabolomics strategy identifies novel inflammatory metabolites in inflammatory bowel diseases. Discovery medicine. 2014; 18(98): 113-24.
17. Jansson J, Willing B, Lucio M, Fekete A, Dicksved J, Halfvarson J, et al. Metabolomics reveals metabolic biomarkers of Crohn's disease. PloS one. 2009; 4(7):e6386.
18. P O B, Vaitheesvaran B, Saha S, Hartil K, Chen E I, Goldman D, et al. Intestinal microbiota-derived metabolomic blood plasma markers for prior radiation injury. International journal of radiation oncology, biology, physics. 2015; 91(2):360-7.
19. De Preter V, Machiels K, Joossens M, Arijs I, Matthys C, Vermeire S, et al. Faecal metabolite profiling identifies medium-chain fatty acids as discriminating compounds in IBD. Gut. 2014.
20. Bakker G C, van Erk M J, Pellis L, Wopereis S, Rubingh C M, Cnubben N H, et al. An antiinflammatory dietary mix modulates inflammation and oxidative and metabolic stress in overweight men: a nutrigenomics approach. The American journal of clinical nutrition. 2010; 91(4): 1044-59.
21. Bouwman J, Vogels J T, Wopereis S, Rubingh C M, Bijlsma S, Ommen B. Visualization and identification of health space, based on personalized molecular phenotype and treatment response to relevant underlying biological processes. BMC medical genomics. 2012; 5:1.
22. Nugent S, Kumar D, Rampton D, Evans D. Intestinal luminal pH in inflammatory bowel disease: possible determinants and implications for therapy with aminosalicylates and other drugs. Gut. 2001; 48(4):571-7.
23. Vernia P, Caprilli R Fau-Latella G, Latella G Fau-Barbetti F, Barbetti F Fau-Magliocca F M, Magliocca Fm Fau-Cittadini M, Cittadini M. Fecal lactate and ulcerative colitis. (0016-5085 (Print)).
24. Tchaptchet S, Fan T-J, Goeser L, Schoenborn A, Gulati A S, Sartor R B, et al. Inflammation-Induced Acid Tolerance Genes gadAB in Luminal Commensal *Escherichia coli* Attenuate Experimental Colitis. Infection and Immunity. 2013; 81(10):3662-71.
25. Li J, Butcher J, Mack D, Stintzi A. Functional impacts of the intestinal microbiome in the pathogenesis of inflammatory bowel disease. Inflamm Bowel Dis. 2015; 21(1):139-53.
26. Dixon L J, Kabi A Fau-Nickerson K P, Nickerson Kp Fau-McDonald C, McDonald C. Combinatorial Effects of Diet and Genetics on Inflammatory Bowel Disease Pathogenesis. (1536-4844 (Electronic)).

What is claimed is:

1. A method of treating or preventing gut barrier dysfunction, an illness associated with gut barrier dysfunction, toxic or inflammatory injury to intestines, or leaky intestinal syndrome in a subject comprising administering to the subject a therapeutic effective amount of a bacterium, wherein the bacterium is *Escherichia coli* genetically engineered to constitutively express tryptophanase, wherein in the presence of tryptophan the bacterium produces indoleacetic acid from tryptophan, and wherein pregnane X receptor (PXR) is activated in apical intestinal epithelial cells, thereby decreasing intestinal permeability and inflammation.

2. The method of claim 1, wherein pregnane X receptor (PXR) is activated in gut apical enterocytes.

3. The method of claim 1, wherein the bacterium is administered orally to the subject.

4. The method of claim 3, further comprising orally administering tryptophan to the subject.

5. The method of claim 1, wherein the subject has irritable bowel syndrome, inflammatory bowel disease, intestinal allergic syndrome or celiac sprue.

6. The method of claim 1, wherein the bacterium colonizes the gut of the subject.

7. The method of claim 1, wherein indoleacetic produced by the bacterium induces target genes of PXR in intestinal mucosa in the subject, wherein the target genes are selected from the group consisting of Multi-drug resistant gene (Mdr 1), Cytochrome P450, family 3, subfamily a, polypeptide 11 (Cyp3a11) and Uridine diphosphate glucuronosyltransferase family 1 member a1 (Ugt1a1).

8. The method of claim 1, wherein indoleacetic produced by the bacterium reduces a mucosal myeloperoxidase enzyme activity in the subject.

9. The method of claim 1, wherein the subject is a human.

10. A method of treating or preventing gut barrier dysfunction, an illness associated with gut barrier dysfunction, toxic or inflammatory injury to intestines, or leaky intestinal syndrome in a subject comprising oral administration to the subject of a therapeutic effective amount of tryptophan and a bacterium, wherein the bacterium is *Clostridium sporogenes* comprising a tryptophanase operon, wherein in the presence of tryptophan, the tryptophanase operon is induced and the bacterium produces indole-3-propionic acid or indoleacetic acid from tryptophan, wherein pregnane X receptor (PXR) is activated in apical intestinal epithelial cells, thereby decreasing intestinal permeability and inflammation.

11. The method of claim 10, wherein pregnane X receptor (PXR) is activated in gut apical enterocytes.

12. The method of claim 10, wherein the subject has irritable bowel syndrome, inflammatory bowel disease, intestinal allergic syndrome or celiac sprue.

13. The method of claim 10, wherein the bacterium colonizes the gut of the subject.

14. The method of claim 10, wherein indoleacetic produced by the bacterium induces target genes of PXR in intestinal mucosa in the subject, wherein the target genes are selected from the group consisting of Multi-drug resistant gene (Mdr1), Cytochrome P450, family 3, subfamily a, polypeptide 11 (Cyp3a11) and Uridine diphosphate glucuronosyltransferase family 1 member al (Ugt1a1).

15. The method of claim 10, wherein indoleacetic produced by the bacterium reduces a mucosal myeloperoxidase enzyme activity in the subject.

16. The method of claim 10, wherein the subject is a human.

* * * * *

SEQUENCE LISTING

<160> NUMBER OF SEQ ID NOS: 20

<210> SEQ ID NO 1
<211> LENGTH: 24
<212> TYPE: DNA
<213> ORGANISM: ARTIFICIAL SEQUENCE
<220> FEATURE:
<223> OTHER INFORMATION: PRIMER DIRECTED TO MOUSE Pxr

<400> SEQUENCE: 1
ctggtcatca ctgttgctgt acca                                    24

<210> SEQ ID NO 2
<211> LENGTH: 26
<212> TYPE: DNA
<213> ORGANISM: Artificial Sequence
<220> FEATURE:
<223> OTHER INFORMATION: primer directed to mouse Prx

<400> SEQUENCE: 2
gcagcatagg acaagttatt ctagag                                  26

<210> SEQ ID NO 3
<211> LENGTH: 23
<212> TYPE: DNA
<213> ORGANISM: Artificial Sequence
<220> FEATURE:
<223> OTHER INFORMATION: PRIMER DIRECTED TO MOUSE Prx

<400> SEQUENCE: 3
ctaaagcgca tgctccagac tgc                                     23

<210> SEQ ID NO 4
<211> LENGTH: 22
<212> TYPE: DNA
<213> ORGANISM: Artificial Sequence
<220> FEATURE:
<223> OTHER INFORMATION: PRIMER DIRECTED TO MOUSE Tlr4

<400> SEQUENCE: 4
atatgcatga tcaacaccac ag                                      22

<210> SEQ ID NO 5
<211> LENGTH: 20
<212> TYPE: DNA
<213> ORGANISM: Artificial Sequence
<220> FEATURE:
<223> OTHER INFORMATION: PRIMER DIRECTED TO MOUSE Tlr4

<400> SEQUENCE: 5
tttccattgc tgccctatag                                         20

<210> SEQ ID NO 6
<211> LENGTH: 22
<212> TYPE: DNA
<213> ORGANISM: Artificial Sequence
<220> FEATURE:
<223> OTHER INFORMATION: PRIMER DIRECTED TO MOUSE Tlr4

<400> SEQUENCE: 6
gcaagtttct atatgcattc tc                                      22

<210> SEQ ID NO 7
<211> LENGTH: 20
<212> TYPE: DNA
<213> ORGANISM: Artificial Sequence

```
<220> FEATURE:
<223> OTHER INFORMATION: PRIMER DIRECTED TO MOUSE Tlr4

<400> SEQUENCE: 7
cctccatttc caataggtag                                                 20

<210> SEQ ID NO 8
<211> LENGTH: 18
<212> TYPE: DNA
<213> ORGANISM: Artificial Sequence
<220> FEATURE:
<223> OTHER INFORMATION: PRIMER DIRECTED TO MOUSE Prx

<400> SEQUENCE: 8
cagtctcttc ccagatgc                                                   18

<210> SEQ ID NO 9
<211> LENGTH: 18
<212> TYPE: DNA
<213> ORGANISM: Artificial Sequence
<220> FEATURE:
<223> OTHER INFORMATION: PRIMER DIRECTED TO MOUSE Prx

<400> SEQUENCE: 9
gtgagggacc attttgtg                                                   18

<210> SEQ ID NO 10
<211> LENGTH: 18
<212> TYPE: DNA
<213> ORGANISM: Artificial Sequence
<220> FEATURE:
<223> OTHER INFORMATION: Primer directed to mouse Prx

<400> SEQUENCE: 10
ggactggtaa tgggtgtc                                                   18

<210> SEQ ID NO 11
<211> LENGTH: 18
<212> TYPE: DNA
<213> ORGANISM: Artificial Sequence
<220> FEATURE:
<223> OTHER INFORMATION: PRIMER DIRECTED TO MOUSE Prx

<400> SEQUENCE: 11
ccatccaacc atctcaag                                                   18

<210> SEQ ID NO 12
<211> LENGTH: 22
<212> TYPE: DNA
<213> ORGANISM: Artificial Sequence
<220> FEATURE:
<223> OTHER INFORMATION: PRIMER DIRECTED TO MOUSE PXR

<400> SEQUENCE: 12
gaggtgtcac tgccatcttc at                                              22

<210> SEQ ID NO 13
<211> LENGTH: 22
<212> TYPE: DNA
<213> ORGANISM: Artificial Sequence
<220> FEATURE:
<223> OTHER INFORMATION: PRIMER DIRECTED TO MOUSE PXR

<400> SEQUENCE: 13
gaggctgctt actctgggtt tt                                              22
```

-continued

```
<210> SEQ ID NO 14
<211> LENGTH: 29
<212> TYPE: DNA
<213> ORGANISM: Artificial Sequence
<220> FEATURE:
<223> OTHER INFORMATION: PRIMER DIRECTED TO MOUSE TLR4

<400> SEQUENCE: 14
gatctctaga aagaaggaac agtgggtac                                    29

<210> SEQ ID NO 15
<211> LENGTH: 29
<212> TYPE: DNA
<213> ORGANISM: Artificial Sequence
<220> FEATURE:
<223> OTHER INFORMATION: PRIMER DIRECTED TO MOUSE TLR4

<400> SEQUENCE: 15
gatctctaga actttcccag gtttcatgg                                    29

<210> SEQ ID NO 16
<211> LENGTH: 17
<212> TYPE: DNA
<213> ORGANISM: MOUSE SP.

<400> SEQUENCE: 16
acttacctga acagagc                                                 17

<210> SEQ ID NO 17
<211> LENGTH: 17
<212> TYPE: DNA
<213> ORGANISM: MOUSE SP.

<400> SEQUENCE: 17
tgaatggact tgtctcg                                                 17

<210> SEQ ID NO 18
<211> LENGTH: 19
<212> TYPE: DNA
<213> ORGANISM: MOUSE SP.

<400> SEQUENCE: 18
aaactttatt gagcaccta                                               19

<210> SEQ ID NO 19
<211> LENGTH: 18
<212> TYPE: DNA
<213> ORGANISM: MOUSE SP.

<400> SEQUENCE: 19
ttgaaataac tcgtggat                                                18

<210> SEQ ID NO 20
<211> LENGTH: 434
<212> TYPE: PRT
<213> ORGANISM: HOMO SAPIENS

<400> SEQUENCE: 20
```

Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
                20                  25                  30

Glu Glu Val Gly Gly Pro Gln Ile Cys Arg Val Cys Gly Asp Lys Ala
            35                  40                  45

```
Thr Gly Tyr His Phe Asn Val Met Thr Cys Glu Gly Cys Lys Gly Phe
 50                      55                  60

Phe Arg Arg Ala Met Lys Arg Asn Ala Arg Leu Arg Cys Pro Phe Arg
 65                  70                  75                  80

Lys Gly Ala Cys Glu Ile Thr Arg Lys Thr Arg Arg Gln Cys Gln Ala
             85                  90                  95

Cys Arg Leu Arg Lys Cys Leu Glu Ser Gly Met Lys Lys Glu Met Ile
            100                 105                 110

Met Ser Asp Glu Ala Val Glu Arg Arg Ala Leu Ile Lys Arg Lys
            115             120                 125

Lys Ser Glu Arg Thr Gly Thr Gln Pro Leu Gly Val Gln Gly Leu Thr
            130                 135                 140

Glu Glu Gln Arg Met Met Ile Arg Glu Leu Met Asp Ala Gln Met Lys
145                     150                 155                 160

Thr Phe Asp Thr Thr Phe Ser His Phe Lys Asn Phe Arg Leu Pro Gly
                165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
            195                 200                 205

Leu Lys Val Ser Leu Gln Leu Arg Gly Glu Asp Gly Ser Val Trp Asn
            210                 215                 220

Tyr Lys Pro Pro Ala Asp Ser Gly Gly Lys Glu Ile Phe Ser Leu Leu
225                     230                 235                 240

Pro His Met Ala Asp Met Ser Thr Tyr Met Phe Lys Gly Ile Ile Ser
                245                 250                 255

Phe Ala Lys Val Ile Ser Tyr Phe Arg Asp Leu Pro Ile Glu Asp Gln
            260                 265                 270

Ile Ser Leu Leu Lys Gly Ala Ala Phe Glu Leu Cys Gln Leu Arg Phe
            275                 280                 285

Asn Thr Val Phe Asn Ala Glu Thr Gly Thr Trp Glu Cys Gly Arg Leu
            290                 295                 300

Ser Tyr Cys Leu Glu Asp Thr Ala Gly Gly Phe Gln Gln Leu Leu Leu
305                     310                 315                 320

Glu Pro Met Leu Lys Phe His Tyr Met Leu Lys Lys Leu Gln Leu His
                325                 330                 335

Glu Glu Glu Tyr Val Leu Met Gln Ala Ile Ser Leu Phe Ser Pro Asp
            340                 345                 350

Arg Pro Gly Val Leu Gln His Arg Val Val Asp Gln Leu Gln Glu Gln
            355                 360                 365

Phe Ala Ile Thr Leu Lys Ser Tyr Ile Glu Cys Asn Arg Pro Gln Pro
370                     375                 380

Ala His Arg Phe Leu Phe Leu Lys Ile Met Ala Met Leu Thr Glu Leu
385                     390                 395                 400

Arg Ser Ile Asn Ala Gln His Thr Gln Arg Leu Leu Arg Ile Gln Asp
                405                 410                 415

Ile His Pro Phe Ala Thr Pro Leu Met Gln Glu Leu Phe Gly Ile Thr
            420                 425                 430

Gly Ser
```